(12) United States Patent
Collazo

(10) Patent No.: US 9,603,605 B2
(45) Date of Patent: Mar. 28, 2017

(54) HIGH TIBIAL OSTEOTOMY GUIDE

(71) Applicant: Howmedica Osteonics Corp., Mahwah, NJ (US)

(72) Inventor: Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 14/012,286

(22) Filed: Aug. 28, 2013

(65) Prior Publication Data

US 2014/0074101 A1    Mar. 13, 2014

Related U.S. Application Data

(60) Division of application No. 11/480,648, filed on Jul. 3, 2006, now Pat. No. 8,545,508, which is a continuation of application No. 11/478,788, filed on Jun. 30, 2006, now Pat. No. 8,241,292, and a continuation of application No. 11/478,790, filed on Jun. 30, 2006, now Pat. No. 8,372,078.

(51) Int. Cl.
| | | |
|---|---|---|
| *A61B 17/15* | (2006.01) | |
| *A61B 17/16* | (2006.01) | |
| *A61B 17/56* | (2006.01) | |
| *A61F 2/28* | (2006.01) | |
| *A61F 2/30* | (2006.01) | |

(52) U.S. Cl.
CPC ........ *A61B 17/152* (2013.01); *A61B 17/1604* (2013.01); *A61B 17/1675* (2013.01); *A61B 2017/565* (2013.01); *A61F 2002/2892* (2013.01); *A61F 2002/30736* (2013.01); *A61F 2002/30892* (2013.01)

(58) Field of Classification Search
CPC ... A61B 17/151; A61B 17/152; A61B 17/809; A61B 17/8095; A61B 17/15
USPC .................................. 606/87, 88, 102, 105
See application file for complete search history.

(56) References Cited

U.S. PATENT DOCUMENTS

| | | |
|---|---|---|
| 683,184 A | 9/1901 | Rockwell |
| 1,661,365 A | 3/1928 | Gendron |
| 1,889,475 A | 11/1932 | Henkel |
| 3,909,889 A | 10/1975 | Emerson |
| 3,977,289 A * | 8/1976 | Tuke ............................. 83/835 |
| 4,409,973 A | 10/1983 | Neufeld |

(Continued)

OTHER PUBLICATIONS

International Search Report, PCT/US2007/014977 dated May 7, 2008.

(Continued)

*Primary Examiner* — Matthew Lawson
*Assistant Examiner* — Amy Sipp
(74) *Attorney, Agent, or Firm* — Lerner, David, Littenberg, Krumholz & Mentlik, LLP

(57) ABSTRACT

A cutting block for use in a bone osteotomy procedure is disclosed, and includes a first cutting guide surface, a second cutting guide surface, and a third cutting guide surface. The first, second, and third cutting guide surfaces are adapted to be temporarily affixed to a bone having a first side and a second side such that the first cutting guide surface is disposed on the first side of the bone, and such that the second cutting guide surface and third cutting guide surface are disposed on the second side of the bone forming an angle therebetween.

20 Claims, 24 Drawing Sheets

(56) References Cited

U.S. PATENT DOCUMENTS

| | | |
|---|---|---|
| 4,421,112 A | 12/1983 | Mains et al. |
| 4,456,006 A | 6/1984 | Wevers et al. |
| 4,483,220 A | 11/1984 | Shindelar |
| 4,509,511 A | 4/1985 | Neufeld |
| 4,565,191 A * | 1/1986 | Slocum .......................... 606/87 |
| 4,608,898 A | 9/1986 | Volk |
| 4,627,425 A | 12/1986 | Reese |
| 4,632,102 A | 12/1986 | Comparetto |
| 4,677,973 A | 7/1987 | Slocum |
| 4,703,751 A | 11/1987 | Pohl |
| 4,750,481 A | 6/1988 | Reese |
| 4,852,558 A | 8/1989 | Outerbridge et al. |
| 4,913,144 A | 4/1990 | Del Medico et al. |
| 5,041,117 A | 8/1991 | Engelhardt |
| 5,053,039 A | 10/1991 | Hofmann et al. |
| 5,112,334 A * | 5/1992 | Alchermes ............ A61B 17/15 606/102 |
| 5,275,603 A | 1/1994 | Ferrante et al. |
| 5,304,180 A | 4/1994 | Slocum |
| 5,413,579 A | 5/1995 | Tom Du Toit |
| 5,449,360 A | 9/1995 | Schreiber |
| 5,540,695 A | 7/1996 | Levy |
| 5,601,565 A | 2/1997 | Huebner |
| 5,613,969 A | 3/1997 | Jenkins, Jr. |
| 5,620,448 A | 4/1997 | Puddu et al. |
| 5,667,511 A | 9/1997 | Vendrely et al. |
| 5,722,978 A | 3/1998 | Jenkins, Jr. |
| 5,749,875 A | 5/1998 | Puddu |
| 5,766,251 A | 6/1998 | Koshino |
| 5,843,085 A | 12/1998 | Graser |
| 5,897,559 A | 4/1999 | Masini |
| 5,911,724 A | 6/1999 | Wehrli |
| 5,980,526 A | 11/1999 | Johnson et al. |
| 6,008,433 A | 12/1999 | Stone |
| 6,059,787 A | 5/2000 | Allen |
| 6,086,593 A | 7/2000 | Bonutti |
| 6,203,546 B1 | 3/2001 | MacMahon |
| 6,261,296 B1 | 7/2001 | Aebi et al. |
| 6,348,054 B1 | 2/2002 | Allen |
| 6,391,031 B1 | 5/2002 | Toomey |
| 6,423,061 B1 | 7/2002 | Bryant |
| 6,544,266 B1 | 4/2003 | Roger et al. |
| 6,575,980 B1 | 6/2003 | Robie et al. |
| 6,575,982 B1 | 6/2003 | Bonutti |
| 6,755,841 B2 | 6/2004 | Fraser et al. |
| 6,796,986 B2 | 9/2004 | Duffner |
| 6,823,871 B2 | 11/2004 | Schmieding |
| 7,083,624 B2 * | 8/2006 | Irving .......................... 606/87 |
| 7,104,996 B2 * | 9/2006 | Bonutti .................... 606/86 R |
| 7,104,997 B2 | 9/2006 | Lionberger et al. |
| 7,572,258 B2 | 8/2009 | Stiernborg |
| 7,901,411 B2 | 3/2011 | Frederick et al. |
| 7,972,338 B2 | 7/2011 | O'Brien |
| 8,192,441 B2 | 6/2012 | Collazo |
| 8,241,292 B2 | 8/2012 | Collazo |
| 8,372,078 B2 | 2/2013 | Collazo |
| 8,545,508 B2 | 10/2013 | Collazo |
| 2002/0164905 A1 | 11/2002 | Bryant |
| 2002/0165552 A1 | 11/2002 | Duffner |
| 2002/0198451 A1 | 12/2002 | Carson |
| 2003/0105526 A1 | 6/2003 | Bryant et al. |
| 2003/0171757 A1 | 9/2003 | Coon et al. |
| 2003/0195516 A1 | 10/2003 | Sterett et al. |
| 2003/0228288 A1 | 12/2003 | Scarborough et al. |
| 2004/0220579 A1 * | 11/2004 | Harwood et al. ............. 606/87 |
| 2005/0021039 A1 | 1/2005 | Cusick et al. |
| 2005/0075641 A1 | 4/2005 | Singhatat et al. |
| 2005/0154394 A1 * | 7/2005 | Michalowicz .................. 606/87 |
| 2005/0234465 A1 | 10/2005 | McCombs et al. |
| 2005/0251147 A1 | 11/2005 | Novak |
| 2005/0273112 A1 | 12/2005 | McNamara |
| 2005/0273114 A1 | 12/2005 | Novak |
| 2006/0052795 A1 * | 3/2006 | White ................ A61B 17/0401 606/102 |
| 2006/0122617 A1 | 6/2006 | Lavallee et al. |
| 2006/0217808 A1 | 9/2006 | Novak et al. |
| 2006/0241636 A1 * | 10/2006 | Novak et al. .................. 606/87 |
| 2007/0016209 A1 | 1/2007 | Ammann et al. |
| 2007/0213830 A1 | 9/2007 | Ammann et al. |
| 2007/0244487 A1 | 10/2007 | Ammann et al. |
| 2007/0265634 A1 | 11/2007 | Weinstein |
| 2008/0015603 A1 | 1/2008 | Collazo |
| 2008/0015604 A1 | 1/2008 | Collazo |
| 2008/0015605 A1 | 1/2008 | Collazo |
| 2008/0140081 A1 * | 6/2008 | Heavener et al. ............. 606/87 |
| 2008/0140213 A1 | 6/2008 | Ammann et al. |
| 2008/0147073 A1 | 6/2008 | Ammann et al. |
| 2008/0147074 A1 | 6/2008 | Ammann et al. |
| 2008/0154267 A1 | 6/2008 | Merchant et al. |
| 2008/0167654 A1 | 7/2008 | Novak et al. |
| 2008/0208197 A1 | 8/2008 | Ammann et al. |
| 2008/0208199 A1 | 8/2008 | Ammann et al. |
| 2008/0243257 A1 | 10/2008 | Taber |
| 2008/0262500 A1 | 10/2008 | Collazo |
| 2009/0018543 A1 | 1/2009 | Ammann et al. |
| 2009/0043308 A1 | 2/2009 | Horacek |
| 2009/0054899 A1 | 2/2009 | Ammann et al. |
| 2009/0076512 A1 | 3/2009 | Ammann et al. |
| 2010/0087824 A1 | 4/2010 | Collazo |

OTHER PUBLICATIONS

CD Newton, Principles and Techniques of Osteotomy, Jan. 1, 1985, IVIS, CH. 40.

Henderson et al., Adolescent tibia vara: alternatives for operative treatment, 1992, JBJS-Am, 74, 342-350.

DK Pal et al., Blount's desease in a patient of Indian lineage—A case report, Apr. 2003, IJO, 37-2.

WB Greene, Infantile tibia vara, 1993, JBJS-Am, 75, 130-143.

Office Action from U.S. Appl. No. 11/478,790, mailed Jun. 10, 2009.

Outerbridge et al., Stryker Howmedica Osteonics Surgical Techniques, High Tibial Osteotomy Using FirstStep Implants and Instruments, 2001.

* cited by examiner

HIGH TIBIAL OSTEOTOMY GUIDE

CROSS-REFERENCE TO RELATED APPLICATIONS

This application is a divisional of U.S. application Ser. No. 11/480,648, filed on Jul. 3, 2006, which is a continuation of U.S. application Ser. No. 11/478,788, filed on Jun. 30, 2006, and U.S. application Ser. No. 11/478,790, filed Jun. 30, 2006, the disclosures of which are incorporated herein by reference.

BACKGROUND OF THE INVENTION

High tibial osteotomy ("HTO") procedures have become well-established means of treating unicompartmental degenerative arthritis of the knee. This condition occurs due to uneven weight bearing of the femoral condyles on either medial or lateral joint compartments of the tibia. Such uneven weight bearing results from either a varus or valgus defect in the tibia. A varus or valgus defect occurs when the mechanical axis of the knee joint shifts either medially (valgus) or laterally (varus) of the preferred location therefor. It is generally accepted that the preferred location for the mechanical axis of the knee is at 62% of the tibial plateau from medial to lateral. The process for determining the location of the mechanical axis is known in the art. A varus deformity generally results in increased loading on the medial joint compartment, while a valgus defect results in increased loading on the lateral joint compartment. A high-tibial osteotomy procedure uses one of various techniques to bring the knee into proper mechanical alignment by correcting a deformity therein, whether varus or valgus. As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

One existing high-tibial osteotomy procedure is what is known as a closing-wedge osteotomy. In such a procedure, a wedge of bone is removed from the tibia and the opening left by the removal is forced closed and secured. The wedge is appropriately shaped to correspond to the appropriate amount of angular correction necessary to bring the knee joint into proper alignment. The procedures for determining both the amount of angular correction and the appropriate wedge shape are known in the art. Generally speaking, however, the wedge is usually shaped so as to span almost the entire medial-lateral width of the tibia, leaving only a narrow "hinge" section of bone on the closed end of the wedge. Once the bone wedge is resected, the opening is forced closed and is typically held in such a position using a staple or other similar device, including bone screws and/or plates. Such procedures are shown in U.S. Pat. No. 5,980,526 to Johnson, et al.; U.S. Pat. No. 6,796,986 to Duffner; U.S. Pat. No. 5,911,724 to Wehrli; U.S. Pat. No. 5,053,039 to Hoffman, et al.; U.S. Pat. No. 5,540,695 to Levy, and; U.S. Pat. No. 5,601,565 to Huebner.

The closing-wedge HTO procedure has several drawbacks. In particular, the approach (when used to correct a varus deformity) requires a transverse cut to be made from the lateral cortex of the tibia across to near the medial cortex thereof through a moderately sized lateral incision. Since the base length of the wedge spans the entire tibial medial-lateral width, the amount of distance to be closed is quite significant, resulting in shortening of the tibia, which may require corresponding shortening of the fibula. It is problematic to shorten the length of the tibia because this can lead to problems in the gait of the patient leading to back, hip or other joint problems, and can complicate any subsequent total knee replacement ("TKR") procedure which may be necessary. Further, if shortening of the tibia requires that the fibula be shortened, the HTO procedure is further complicated and patient pain and recovery time are increased. Additionally, tibial shortening leads to a significant amount of soft tissue laxity of the lateral compartment, which includes the joint capsule, lateral collateral ligament, etc. Other complications arise from a closing wedge HTO procedure because the resected tibial plateau is "hinged" medially, for example. This can result in the resected joint being extremely unstable during healing. Subsequent TKR is further complicated by the presence of the staple used to secure the joint during healing because the staple may have to be removed prior to TKR.

An alternative procedure is the opening wedge HTO. In this procedure, a single cut is made from, for example, the medial cortex of the tibia across to near the lateral cortex in order to correct a varus defect (to correct a valgus defect a cut is made from the lateral cortex to near the medial cortex). As with closing wedge HTO, the cut in an opening wedge HTO procedure extends through almost the entire tibia, leaving only enough bone on the lateral tibia to form a hinge section. The cut is then forced open to form a wedge having an angle corresponding to the required amount of angular correction. This procedure can also be used to correct a valgus defect, with the cut originating on the lateral tibia, extending through the tibia to near the lateral tibia. Once the cut is opened, an appropriately shaped wedge can be inserted into the cut to support the tibial plateau at the desired angle. The wedge can be made of a known bone-substitute material, an autograft taken from the patient's iliac crest or an allograft taken from a donor. The wedge is then secured in place using hardware typically in the form of bone plates and screws.

Various disadvantages to the opening wedge HTO exist as well. Specifically, the amount of the distance to be "opened" can be quite significant, leading to lengthening of the leg and an undesirable amount of soft tissue tensioning of, for example, the medial compartment, which includes the joint capsule, the medial collateral ligament, etc. Furthermore, the lateral or medial hinging of the osteotomy makes it extremely unstable, due to the amount of leverage applied to the hinge section from the opposite side of the tibia. This instability makes the knee unable to resist torsional loads applied to the joint. Therefore, it is necessary to secure the cut with bulky plates and/or screws in order to stabilize the joint while it heals. The presence of such hardware can complicate any subsequent TKR procedure which may be required. Additionally, due to the large size of the wedge inserted into the cut, resorption and incorporation of a bone substitute device that may be used to fill the wedge is lengthy. While it is preferred that the wedge be made from autograft material, which is usually removed from the iliac crest of the patient. This harvesting requires a separate procedure to be performed to harvest the autograft, which adds time, pain, blood loss and the risk of infection to the procedure. Therefore various allograft implants have been designed to fill the wedge as illustrated in U.S. Pat. No. 6,575,982 to Bonutti, and in U.S. Pat. Pub. No. 2005/0075641 to Singhatat, et al. These implants generally are made of a biologically compactable material and may include features to promote affixation to the bone and/or bony ingrowth. Alternatively, the wedge can be left unfilled, the tibial plateau being supported by plate or bracket such as those shown in U.S. Pat. No. 6,823,871 to Schmieding and U.S. Pat. Pub. No. 2003/0195516 to Sterett.

Various tools have been developed in order to facilitate both the opening and closing wedge osteotomy procedure. Typically, these include cutting guide surfaces which are capable of being affixed to the bone and provide a surface which is used to guide a bone saw or other known instrument into proper alignment for the desired cut or cuts. Typically, these guides are designed to affix to either the medial or lateral side of the tibia, depending on the type of correction required and the procedure used. By taking either a medial or lateral approach for cutting, the patellar tendon is easily avoided; however, these approaches make alignment of cuts more difficult, because the mechanical axis is not visible from the side of the knee.

A further alternative procedure known in the art is a dome tibial osteotomy. In this procedure, the entire proximal tibia, as well as the proximal fibula are detached from the remaining tibia using a curved or dome-shaped bone cut. The proximal tibia is then repositioned in the correct alignment and secured in place with various forms of hardware, which can include staples, plates, screws, or cerclage wire. The total bisection of both the proximal tibia and fibula leads to an extremely unstable joint, which requires a great deal of hardware for stabilization, which would, most likely, need to be removed prior to subsequent TKR. This procedure is advantageous because it neither shortens nor lengthens the leg to a problematic extent. However, it is generally regarded as too invasive or risky for practical purposes.

SUMMARY OF THE INVENTION

The present invention relates to a cutting block for use in a bone osteotomy procedure. The cutting block includes a first cutting guide surface, a second cutting guide surface, and a third cutting guide surface. The first, second, and third cutting guide surfaces of the cutting block are adapted to be temporarily affixed to a bone having a first side and a second side such that the first cutting guide surface is disposed on the first side of the bone, and such that the second cutting guide surface and third cutting guide surface are disposed on the second side of the bone forming an intersecting angle therebetween.

The first and second cutting guide surfaces of the cutting block may be disposed on a first arm of the cutting block, and the third cutting guide surface disposed on a second arm of the cutting block. In such an arrangement, the second arm is preferably rotatably affixed to the first arm. The first cutting guide surface and the second cutting guide surface are preferably disposed on the first arm in a parallel relationship to each other such that the first cutting guide surface is located proximally of the second cutting guide surface. In such an embodiment, the first cutting guide surface is used to form a first cut in the proximal tibia, the second cutting guide surface is used to form a second cut in the proximal tibia, and third cutting guide surface is used to form a third cut in the proximal tibia. Each of these cuts has a terminal end, and the terminal ends of the first and second cuts form an overlap therebetween.

An alternative embodiment of the present invention relates to a cutting block for use in a high-tibial osteotomy procedure. The cutting block is preferably adapted to be temporarily affixed to an anterior portion of a proximal tibia having a first side and a second side. The first and second sides may be either the lateral or medial sides of the tibia. The cutting block includes a body having a first cutting guide surface and a receiving portion formed therein. Preferably, the first cutting guide surface is disposed substantially on the first side of the proximal tibia. The cutting block further includes first and second interchangeable portions, which are adapted to be selectively inserted within the receiving portion of the body. A second cutting guide surface is positioned in the first interchangeable portion such that when the first interchangeable portion is inserted within the receiving portion, the second cutting guide surface is disposed substantially on the second side of the proximal tibia and is parallel to the first cutting guide surface. A third cutting guide surface is positioned within the second interchangeable portion such that when the second interchangeable portion is inserted within the receiving portion, the third cutting guide surface is disposed substantially on the second side of the proximal tibia and forms an obtuse angle relative to the first cutting guide surface.

A further embodiment of the present invention relates to a system for performing a bone osteotomy procedure. The system includes a first cutting block having a first cutting guide surface formed therein. The first cutting block is adapted to be affixed to the bone in a first position such that the cutting guide surface is disposed substantially on a first side of the bone and a second position such that the first cutting guide surface is disposed substantially on a second side of the bone and is located distally of the first position. The system further includes a second cutting block having a second cutting guide surface formed therein and being adapted for affixation to the bone such that the second cutting guide surface is positioned relative to the first position of the first cutting guide surface such that it forms an intersecting angle therewith.

A still further embodiment of the present invention relates to a system for performing a high-tibial osteotomy procedure. The system includes a first cutting block having a first cutting guide surface formed therein. The first cutting block is adapted to be affixed to an anterior surface of a proximal portion of the tibia in a first position such that the cutting guide surface is disposed substantially on a first side of the tibia and a second position such that the first cutting guide surface is disposed substantially on a second side of the tibia and is located distally of the first position. The system further includes a second cutting block having a second cutting guide surface formed therein. The second cutting block is adapted for affixation to the anterior surface of the proximal portion of the tibia such that the second cutting guide surface is positioned relative to the first position of the first cutting guide surface such that it forms an intersecting angle therewith.

An embodiment of the present invention further includes a method for performing an osteotomy procedure on a bone having a first side and a second side. The method includes making a first cut in the bone extending in a first direction from an outside surface on the first side of the bone to a first line being disposed within the bone and extending in a second direction orthogonal to the first direction substantially through the bone. The method also includes making a second cut in the bone extending in a first direction from an outside surface on the second side of the bone to a second line being disposed within the bone and extending in a second direction orthogonal to the first direction substantially through the bone. The second cut is spaced apart from the first cut along a longitudinal axis of the bone. The method further includes making a third cut in the bone extending in a first direction from an outside surface on the first side of the bone to a third line near being disposed within the bone and extending in a second direction orthogonal to the first direction substantially through the bone. The first cut and third cut form an intersecting angle therebetween along the respective first directions thereof such that an apex is formed along a the third line.

A further embodiment of the present invention includes a method for performing a high tibial osteotomy. The method includes making a first cut in a proximal tibia in a first plane, and making a second cut in a proximal tibia in a second plane. The first and second planes are spaced in a proximal-distal direction. The method further includes making a third cut in the proximal tibia in a third plane. The third plane is at an angle with and intersecting one of said first and second planes. The first, second and third cuts open to a medial or lateral side of the proximal tibia. The method also includes removing a bone wedge formed by the intersection of the third cut with one of the first or second cuts. Additionally, the method includes closing a wedge shaped opening formed by the removal of the bone wedge by rotating the proximal tibia about an anterior to posterior axis to open the one of the first and second cuts not intersecting with the third cut. The method further includes inserting the bone wedge into one of the first and second bone cuts opened by the rotation about the anterior-posterior axis.

BRIEF DESCRIPTION OF THE DRAWINGS

The present invention will be better understood on reading the following detailed description of nonlimiting embodiments thereof, and on examining the accompanying drawings, in which.

DETAILED DESCRIPTION

In describing the preferred embodiments of the subject matter illustrated and to be described with respect to the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

Figure 1:
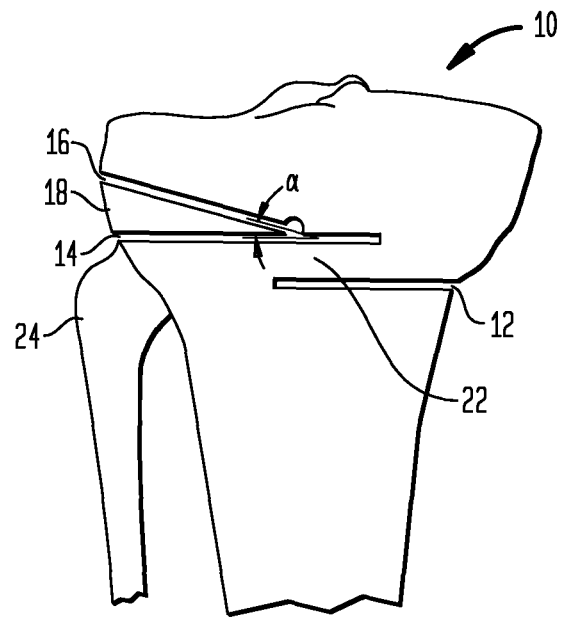
FIG. 1 is an anterior view of a proximal tibia during a step of a procedure showing three bone cuts according to an embodiment of the present invention.

Referring to the drawings, wherein like reference numerals represent like elements, there is shown in FIGS. 1-4, in accordance with one embodiment of the present invention, an anterior view of the right tibia 10 with a series of cuts which can be used to complete an HTO procedure. The illustration in FIG. 1 shows exemplary locations for cuts in an HTO procedure used to correct a varus defect on the proximal tibia 11; however, as would be understood by one having reasonable skill in the art upon reading this disclosure, the procedure of the present invention can also be used to correct a valgus defect. As shown in FIG. 1, first cut 12 extends in the medial-lateral direction from the medial cortex of the tibia toward the centerline of the tibia. Preferably, first cut 12 extends in the medial-lateral direction to a terminus that is lateral of the centerline of the tibia. First cut 12 extends in the anterior-posterior direction from the anterior tibial cortex through the posterior cortex. Second cut 14 extends in the medial-lateral direction from the lateral cortex toward the centerline of the tibia. Preferably, second cut 14 extends to a terminus that is medial of the centerline of the tibia such that overlap 22 is formed between first cut 12 and second cut 14. Preferably, first and second cuts 12, 14 are perpendicular to the mechanical axis of the tibia. Additionally, second cut 14 is preferably proximal to first cut 12. Third cut 16 extends in the medial-lateral direction from the lateral cortex of the tibia toward the centerline of the tibia at an angle relative to second cut 14 so as to form autograft 18, having a wedge shape, therebetween. The angle α between third cut 16 and the second cut 14 corresponds with the amount of angular correction determined to be necessary for the knee. As previously stated, the procedure of the current invention can be used to correct either a varus or valgus defect in the tibia. The location and placement of first, second and third cuts 12, 14, 16 will vary depending on which of these defects is being treated. For example, FIG. 1 shows a varus defect on the right tibia which is treated by forming second and third cuts 14, 16 on the lateral side of the proximal tibia 11. Conversely, if a valgus defect is treated, second and third cuts 14, 16 are formed on the medial side of proximal tibia 11, and first cut 12 is formed on the lateral side thereof. As shown in FIG. 1, the procedure of the present embodiment is particularly useful in treating a varus defect wherein second cut 14 is located proximal of the fibular head 24, which may prevent the need for a distraction thereof during the procedure. When making reference to first, second and third cuts 12, 14, 16 throughout this disclosure, it is noted that the ordinal reference is made only for convenience and relates only to a preferred order in which cuts are made in accordance with one embodiment of the present invention. While it is preferred that first, second and third cuts 12, 14, 16 are made in order of reference, it is to be understood that first, second and third cuts can be made in any order.

Figure 2:
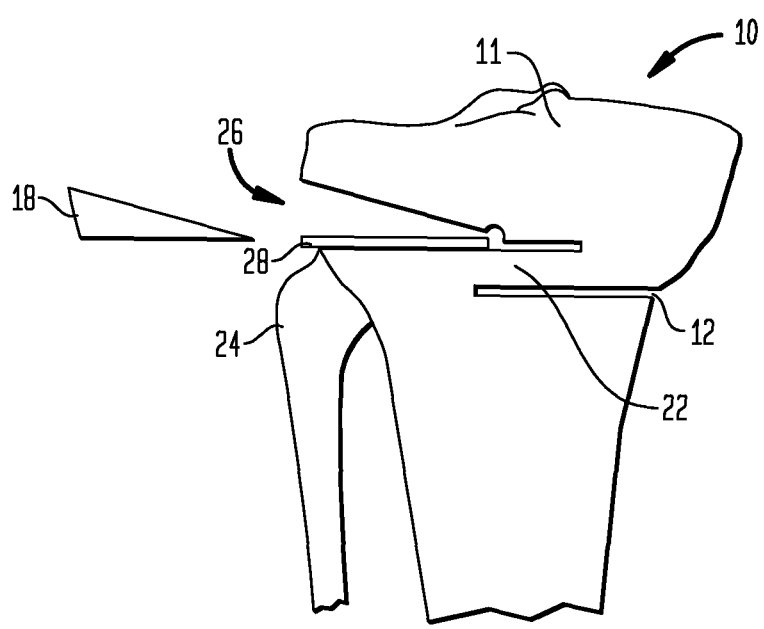
FIG. 2 is an anterior view of a proximal tibia showing removal of a bone wedge made by two of the cuts of FIG. 1.
Figure 3:
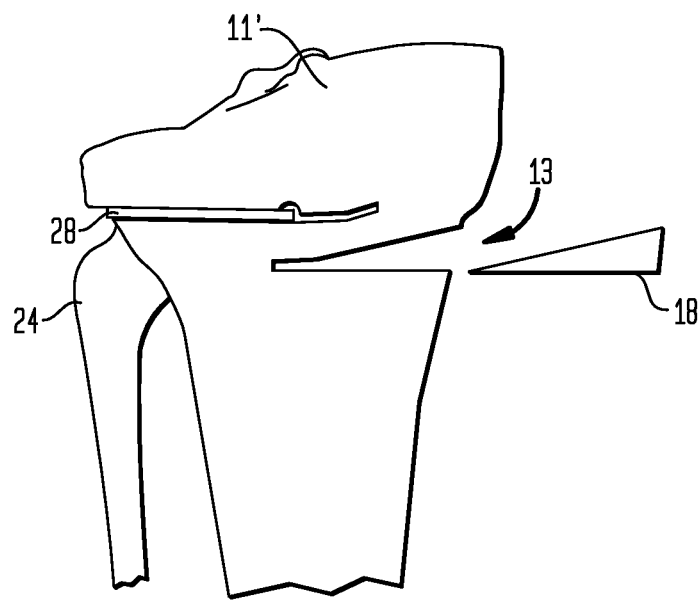
FIG. 3 is an anterior view of a proximal tibia during a step of a procedure showing the insertion of the bone wedge of FIG. 2 in the third cut of FIG. 1.

In a preferred method for performing an HTO procedure according to an embodiment of the present invention, first cut 12 is made in tibia 10, followed by second cut 14 and third cut 16, respectively. As shown in FIG. 2, once first, second and third cuts 12, 14, 16 have been made, autograft 18 is removed from tibia 10 to form closing wedge 26. Then, the tibial plateau 11 is rotated so as to close closing wedge 26 while expanding first cut 12 to form open wedge 13, as shown in FIG. 3. Preferably, as shown in FIG. 2, filler implant 28 is inserted into closing wedge 26 prior to rotation of the tibial head 11.

Figure 5:
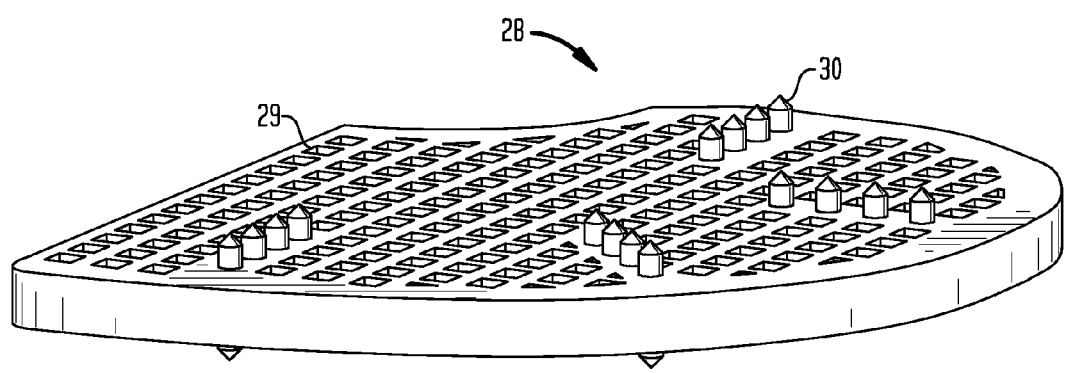
FIG. 5 is an isometric view of a filler implant for insertion into area of the tibia from which the bone wedge has been removed, as seen in FIGS. 2-4.

A filler implant 28 is shown in FIG. 5; the preferred filler implant 28 is generally planar in shape with a profile designed to generally match the profile of the area to which it is inserted. The thickness of implant 28 should be such that it can compensate for the material removed from the bone due to the cutting of the bone. Depending on the specific procedure used to make the required cuts in the bone, the thickness of filler implant 28 may need to be either approximately that of one saw blade or of two saw blades. Furthermore, the preferred implant 28 has a substantially porous structure comprising a plurality of openings 29 to allow for bone ingrowth during the healing process after the procedure. In order to increase stability of the knee joint during the healing process, implant 28 can further have a surface designed to increase the friction between the interior surfaces of the knee and the surface of the implant 28. This can include having fixation protrusions 30 extend from implant 28. The insert may be made of metal or a bioabsorbable material such as polylactide-glycolide polymer. The insert may be coated with an osteoinductive or osteoconductive material such as hydroxyapatite and/or BMPs such as OP-I.

Figure 4:
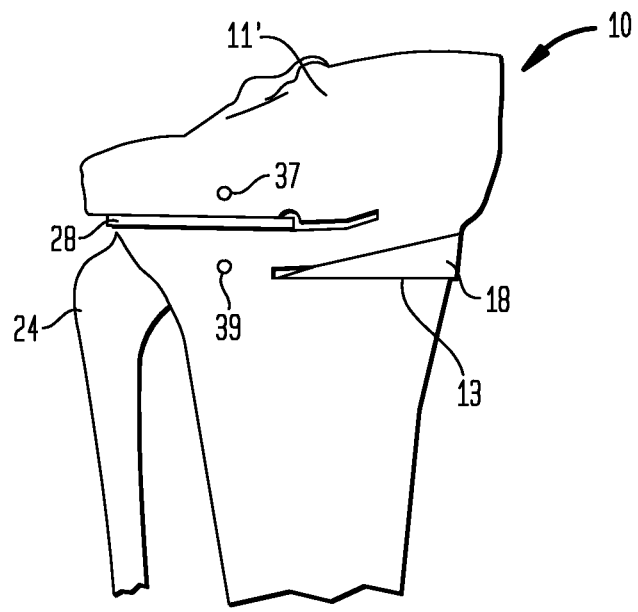
FIG. 4 is an anterior view of a proximal tibia after insertion of the bone wedge of FIG. 3.

Referring now to FIG. 4, once opening wedge 13 has been formed from the first cut 12, autograft 18 is inserted into opening wedge 13 to thereby provide the required amount of angular correction to form a properly-oriented plateau 11' of the tibia 10. The procedure for determining the appropriate amount of angular correction in such a procedure is well-known in the art. Finally, a well-known adjustable staple or clamping device (not shown) is placed in holes 37, 39 formed both proximally and distally of closing wedge cuts 14, 16, and a compressive load is applied to the bone to prevent movement thereof while healing occurs. Examples of such devices are shown in U.S. Pat. No. 4,913,144 to Del Medico, and U.S. Pat. No. 4,852,588 to Outerbridge.

Figure 6:
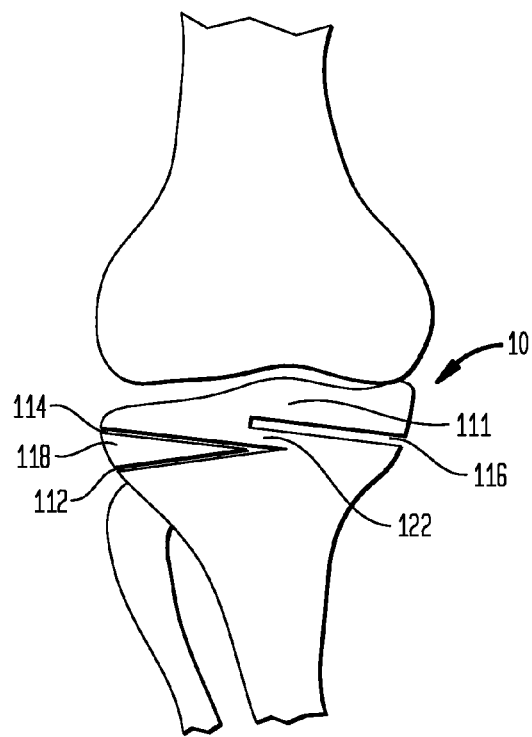
FIG. 6 is an anterior view of a proximal tibia during a step of a procedure showing three bone cuts according to a second embodiment of the present invention.
Figure 7:
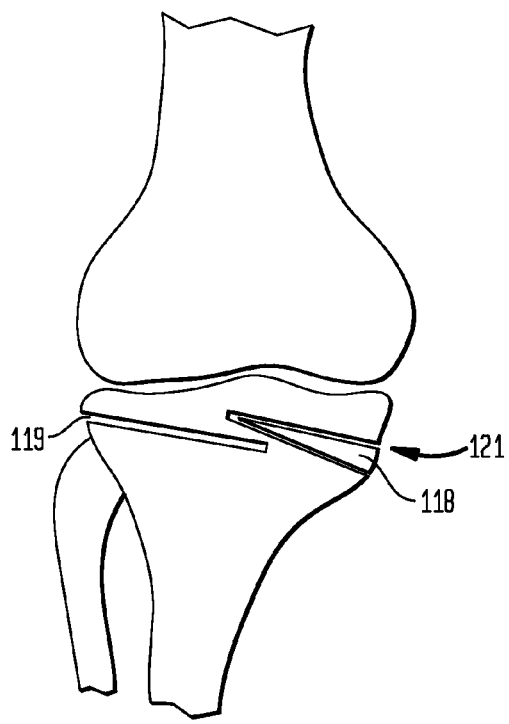
FIG. 7 is an anterior view of a proximal tibia showing the bone wedge made in FIG. 6 moved from one side to the other.

FIGS. 6 and 7 depict an alternative arrangement for first, second and third cuts 112, 114, 116 as used in correction for a varus defect in tibia 110. A method for performing an HTO procedure according to this embodiment of the present invention includes making first cut 112 in the tibia 10 near the proximal end 11 thereof so as to extend in the medial-lateral direction from the lateral cortex of the tibia toward the centerline thereof. Second cut 114 is then formed in tibia 10 proximal of first cut 112 extending in the medial-lateral direction from the lateral cortex toward the centerline of the tibia 10. Preferably, both first cut 112 and second cut 114 extend medially of the centerline of the tibia 110. Second cut 114 is formed at an angle relative to first cut 112 and extends to intersect first cut 112 so as to form a removable wedge-shaped autograft 118 therebetween. Third cut 116 is formed in tibia 110 preferably proximally of second cut 114 extending in the medial-lateral direction from the medial cortex of tibia 110 toward the centerline of tibia 110. Preferably, third cut 116 extends to a terminus that is lateral of the centerline of tibia 110 so as to form an overlap 122 between first cut 112 and third cut 116. The distance between third cut 116 and second cut 114 in the proximal direction should be appropriate for overlap portion 122 to form a hinge between tibial head 111 and the remaining portion of the tibia 110. Autograft 118 is extracted from tibia 110 to form closing wedge 119. The tibial head 11 is then rotated to close closing wedge 119 and open opening wedge 121 from third cut 116. Autograft 118 is then inserted into opening wedge 121. The resected joint is then secured using staples or clamps as discussed with respect to FIGS. 1-4. As previously discussed, FIGS. 6-7 depict a pattern for first second and third cuts 112, 114, 116 used to correct a varus deformity in the knee; however, it is understood that the method of the present embodiment can be used to correct a valgus deformity by forming first and second cuts 112, 114 in tibia 110 so as to originate on the medial side of tibia 110, and to form third cut 116 so as to originate on the lateral side of tibia 110. This embodiment of the present invention is particularly useful when correcting a valgus defect because it allows for opening wedge 12 to be positioned proximal of the fibular head 24. As discussed with reference to FIGS. 1-5, implant 28 can be inserted into closing wedge 119 prior to rotation of the tibial head. Implant 28 is structured to compensate for the loss of bone material due to the thickness of the cutting instrument used in formation of the cuts and to provide stability for the joint during healing.

Figure 8:
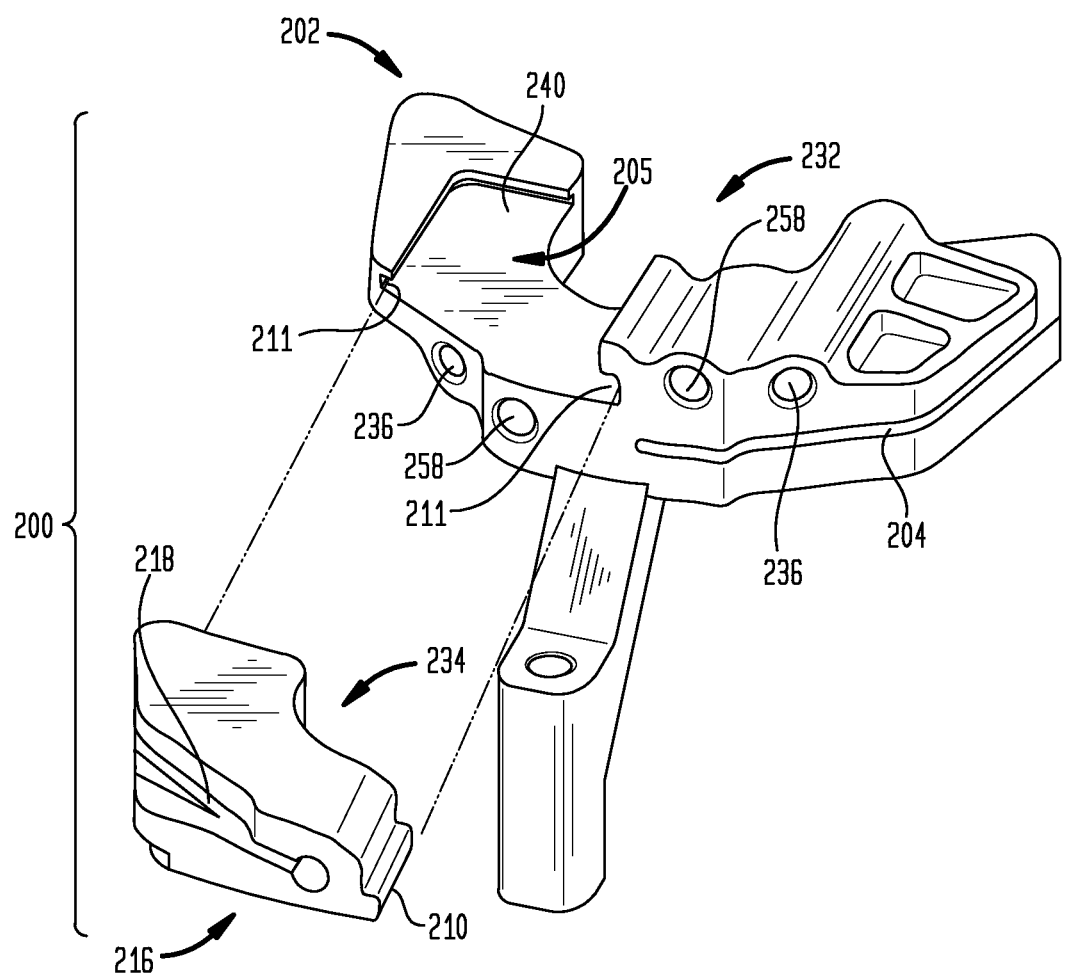
FIG. 8 is an isometric view of a first embodiment of a cutting block according to an embodiment of the present invention showing a removable insert.

Referring now to FIG. 8, an embodiment of a cutting block that can be used to aid in forming first, second and third cuts 12, 14, 16 for an HTO procedure according to an embodiment of the present invention is shown. In describing preferred embodiments of the cutting block of the present invention, reference will be made to directional nomenclature used in describing the human body. It is noted that this nomenclature is used only for convenience and that it is not intended to be limiting with respect to the scope or structure of the invention. When referring to specific directions, the device is understood to be described only with respect to its orientation and position during an exemplary application to human body.

Figure 9:
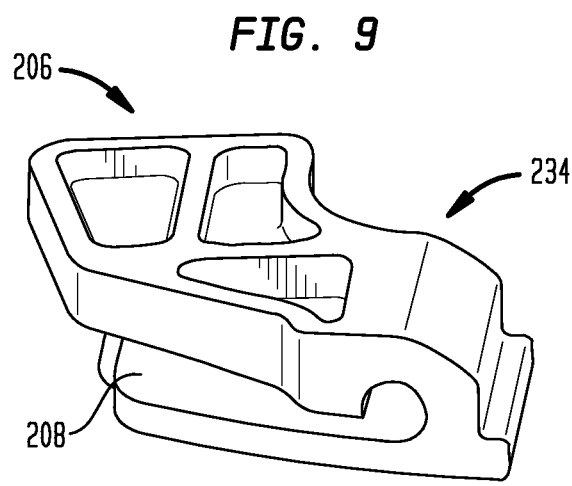
FIG. 9 is an isometric view of the insert for the cutting block of FIG. 8.
Figure 10:
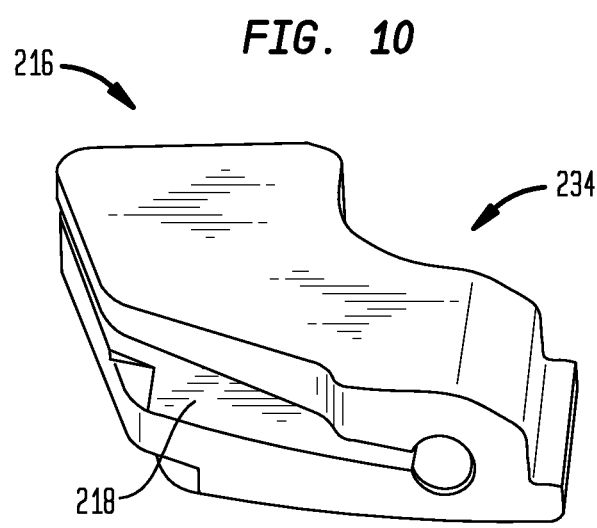
FIG. 10 is an isometric view of an alternative insert for use with the cutting block of FIG. 8.
Figure 11:
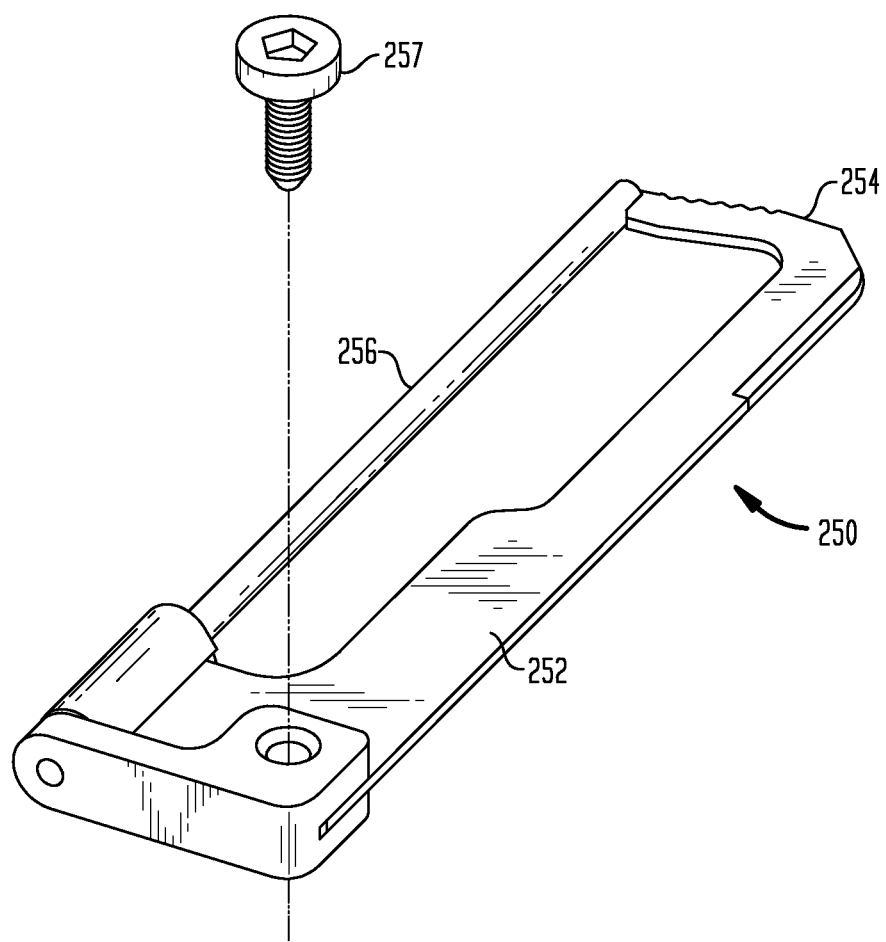
FIG. 11 is an isometric view of an osteotome according to an embodiment of the present invention.

As shown in FIG. 8, a preferred cutting block 200 according to one embodiment of the present invention includes body 202 which has a first guide surface 204 formed therein. The particular embodiment of cutting block 200 shown in FIG. 8 is preferably used to form the cutting pattern shown in FIGS. 1-4, but it would be understood by one of reasonable skill in the art upon reading this disclosure that cutting block 200 shown in FIG. 8 could be modified to form other arrangements for cutting patterns used in HTO procedures according to alternative embodiments of the present invention. Returning now to FIG. 8, in the exemplary embodiment illustrated, cutting block 200 is adapted to be affixed to the anterior portion of the proximal tibia, first guide surface 204 being positioned on the medial side of body 202. First guide surface 204 is preferably adapted to form first cut 12 (FIG. 1). Body 202 further includes a receiving portion 205, which is adapted to receive a first cutting guide insert 206 (FIG. 9) or second insert 216 (FIG. 10) therein. First insert 206 is preferably used to form second cut 14 according to the method of the present invention discussed with reference to FIGS. 1-4. Accordingly, first insert 206 has second guide surface 208 formed therein such that when first insert 206 is inserted into receiving portion 205, second guide surface 208 is substantially parallel to first guide surface 204 and located proximally thereto. In the preferred embodiment, the guide surfaces are in the form slots formed in body 202. In preferred embodiment, insert 206 includes flange 210 formed in the outer periphery of the lower portion thereof so as to correspond with a groove 211 formed around the outer periphery of receiving portion 205. Second insert 216 is preferably adapted to be used in forming third cut 16, as described with reference to FIGS. 1-4. Accordingly, second insert 216 has third guide surface 218 formed therein such that when second insert 216 is engaged within receiving portion 205 third guide surface 218 is appropriately angled and positioned relative to first guide surface 204 to form third cut 16. Second guide 216 is adapted for engagement within receiving portion 205 in a similar fashion as with respect to first insert 206.

Cutting block 200 is formed of a material sufficient to give cutting block 200 an appropriate rigidity to accurately guide a cutting instrument for formation of the cuts necessary for the HTO procedure. Preferably, cutting block 200 is made from a material that allows for multiple uses, which includes the ability to be repeatedly subjected to the various sterilization procedures used in the art. Acceptable materials for cutting block 200 include, but are not limited to, surgical steel, titanium or other similar materials.

As shown in FIGS. 11-18, a further embodiment of the present invention includes a method for performing an HTO procedure according to a particular embodiment of the present invention using cutting block 200. This method includes forming an incision near the knee of the patient suitable for introduction of cutting block 202 to the anterior proximal tibia. In an alternative embodiment of the present invention, two incisions can be made in the knee area of the patient, one lateral of the patella tendon and one medial of the patella tendon. The incision is then retracted and body 202 of cutting block 200 is introduced to the proximal portion tibia 10. Body 202 of cutting block 200 is then positioned such that the lateral plane 240 (FIGS. 8, 11-13) of insert portion 205 is preferably just proximal to the fibular head 24 (shown in FIG. 1). An alignment rod 244 is then placed into alignment rod hole 242 which is affixed to body 202 of the cutting block 200. Alignment rod 244 is used to align cutting block 200 with the mechanical axis of the tibia, which is typically in the varus-valgus and flexion-extension about the distal end of the tibia. Holes are then drilled in proximal tibia using guide holes 236 in body 202. Fixation pins 246 are then inserted into the proximal tibia through guide holes 236 in order to maintain body 202 in the appropriate position on tibia 210. Once alignment and fixation are achieved, alignment rod 244 is then removed from hole 242.

Figure 12:
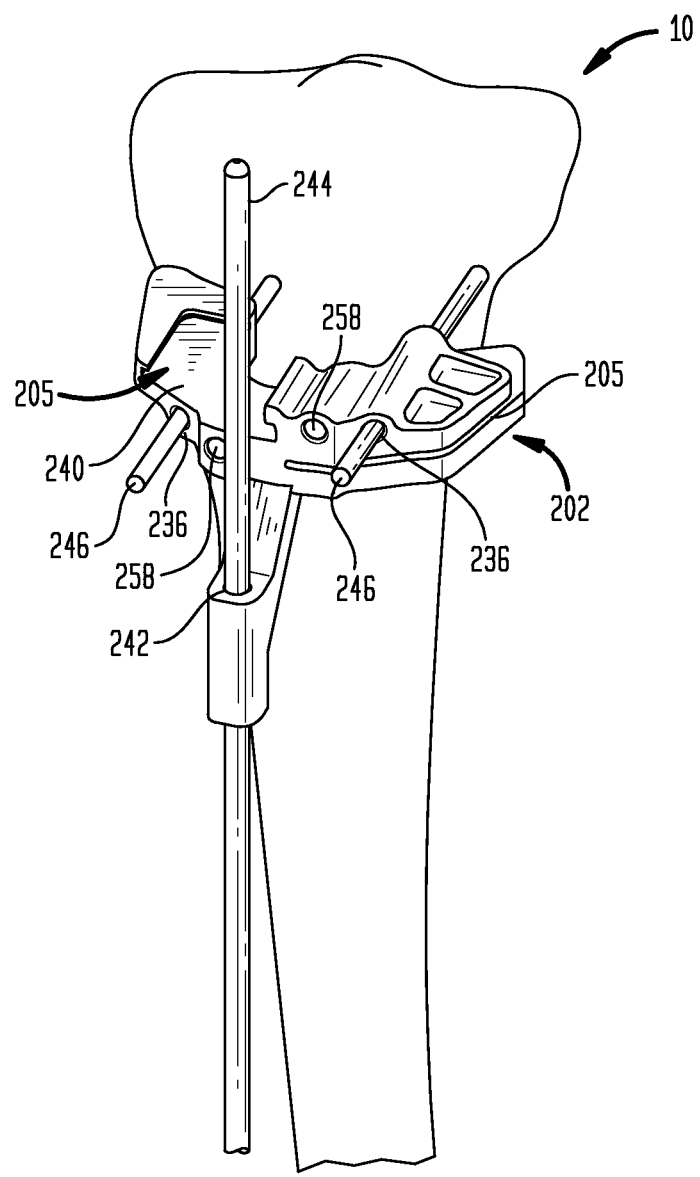
FIG. 12 is an isometric view of a tibia with the cutting block of FIG. 8 mounted thereto during step in a process according to an embodiment of the present invention.
Figure 13:
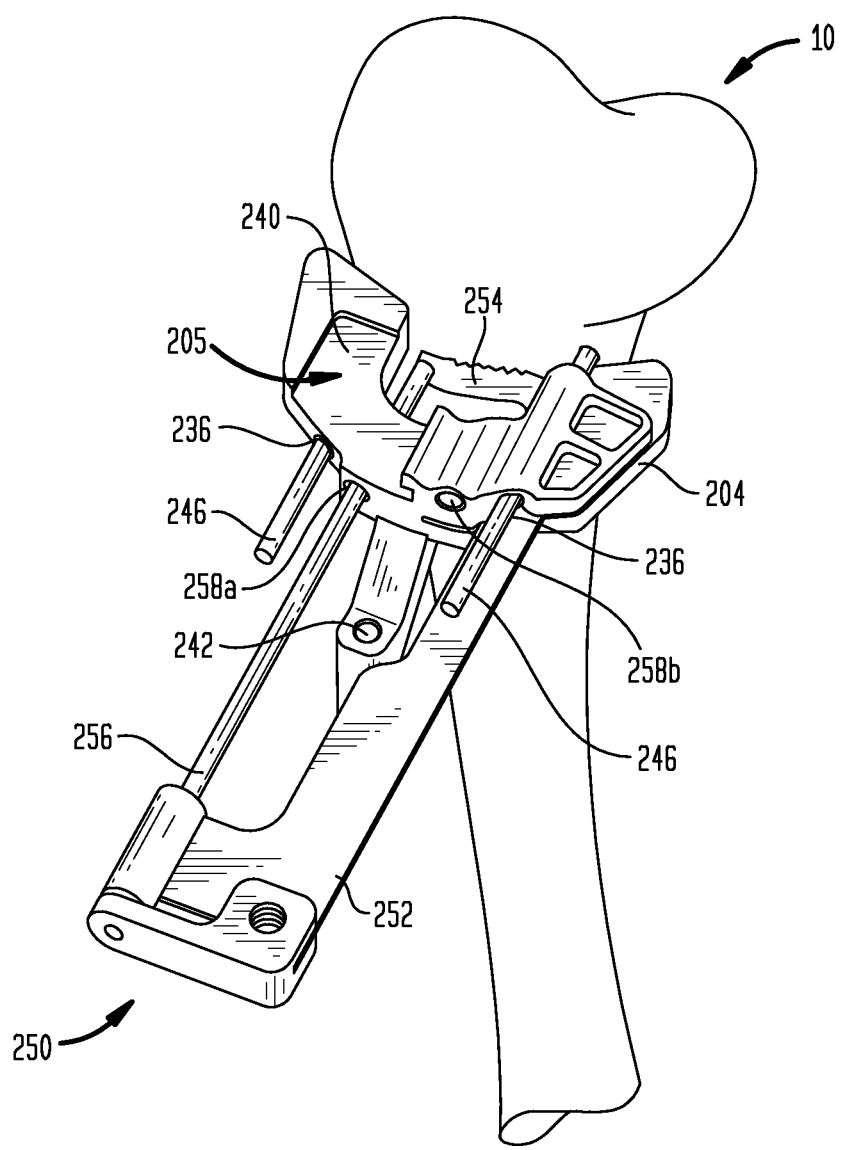
FIG. 13 is an isometric view of a tibia with the cutting block of FIG. 8 mounted thereto and the osteotome of FIG. 11 inserted therein to form a first cut during step in a process according to an embodiment of the present invention.
Figure 18:
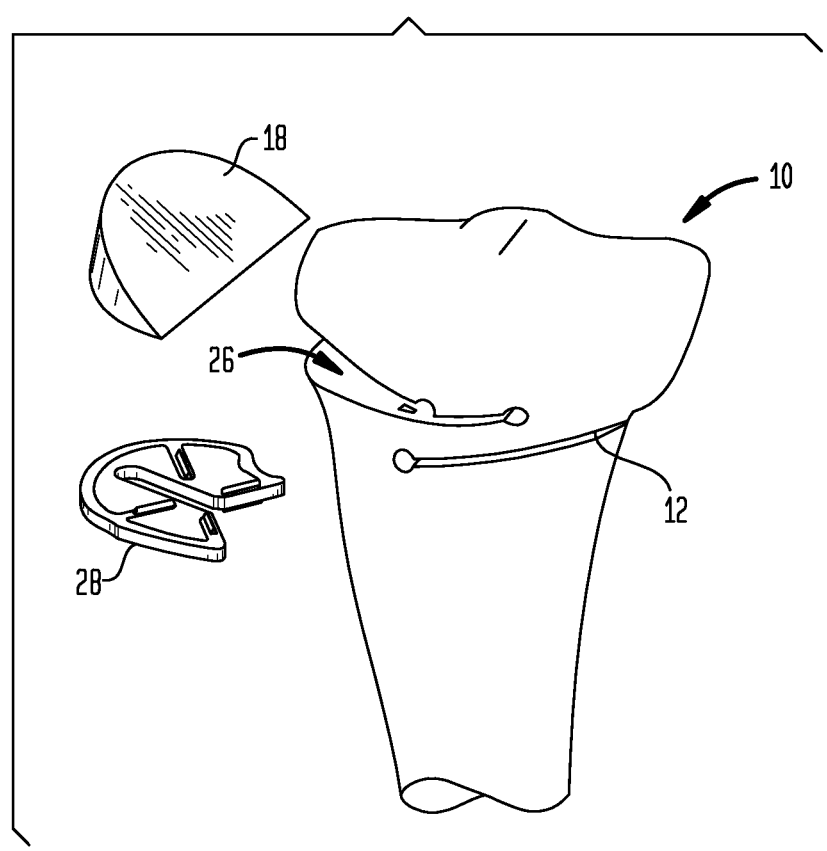
FIG. 18 is an isometric view of a tibia during step in a process showing the removal of the bone wedge prior to insertion of a filler implant.

When using an anterior approach to the proximal tibia in performing an osteotomy procedure according to the current embodiment of the present invention, while a saw blade can be used to start cuts 12, 14, interference with the patella tendon of the patient prevents a straight bone saw as it is known in the art from being used to complete cuts 12, 14 of an appropriate width for completion of the procedure. Accordingly, an osteotome 250 as shown in FIG. 12, having generally an L-shaped cutting portion, is used in this procedure. Osteotome 250 has a body portion 252 and a cutting portion 254 structured such that body portion 252 extends through cutting guide surface and allows cutting portion 254 to reach behind the patella tendon so that the necessary cuts can be completed, as shown in FIG. 13. Preferably, osteotome has a guide arm 256 that provides further support for cutting portion 254 and further mates with guide holes 258 formed in body 202 of cutting block 200. Guide arm 256 is preferably affixed to body portion 252 using screw 257. When such an ostetome is used, the method according to the current embodiment of the present invention includes the step of drilling a corresponding guide hole 259 in the proximal tibia using guide hole 258. These holes 259 are shown in FIG. 18. Preferably, osteotome 250 is structured such that guide holes 259 are formed at the terminal ends of first, second and third cuts 12, 14, 16. Such an arrangement not only provides for further guidance of osteotome 250 within tibia 10, but also reduces the stress concentration within the bone which would be present at the terminal end of a cut without such a hole. Removal of stress concentrations is preferred because stress concentrations may lead to formation of cracks within the bone during rotation of the tibial head or during healing.

Figure 14:
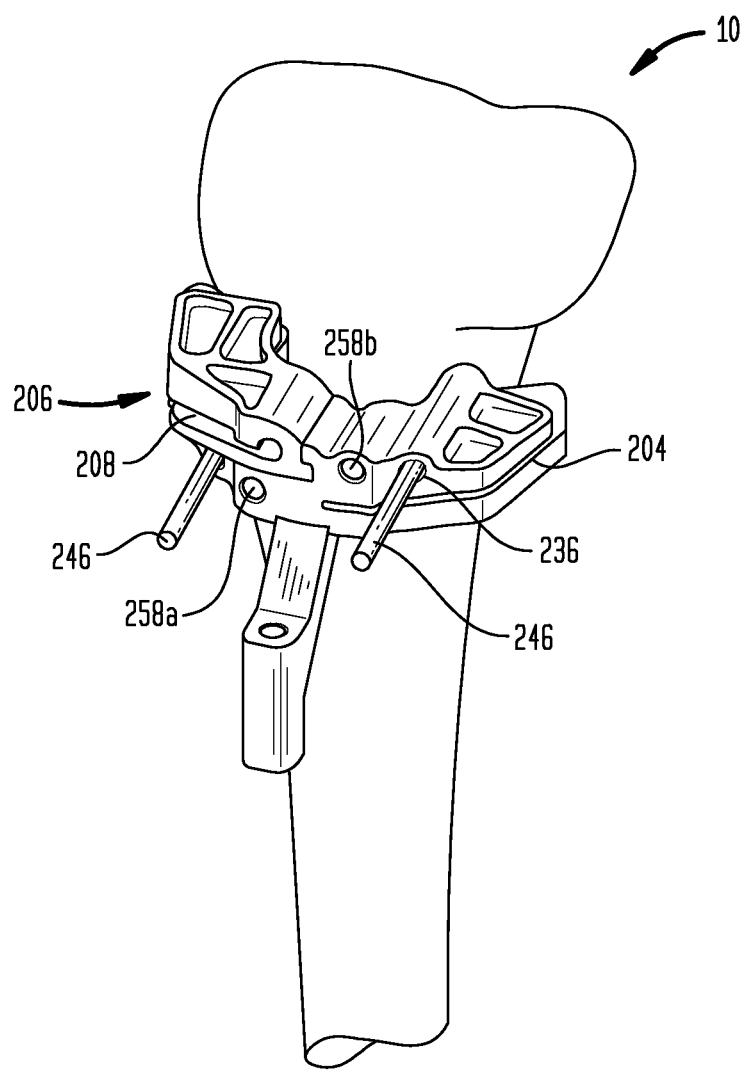
FIG. 14 is an isometric view of a tibia with the cutting block of FIG. 8 mounted thereto during step in a process according to an embodiment of the present invention.
Figure 15:
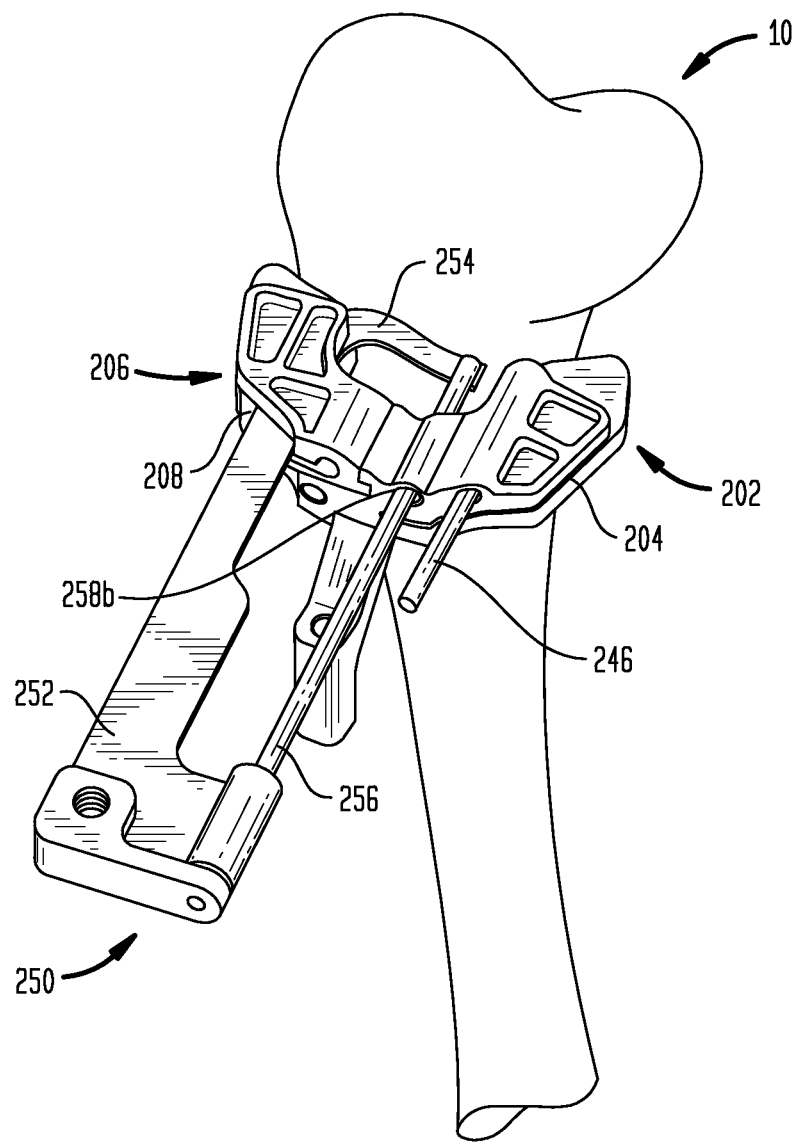
FIG. 15 is an isometric view of a tibia as shown in FIG. 14 with the osteotome of FIG. 11 used to finalize a second cut in the tibia.

In the preferred method, first cut 12 is partially formed in the proximal tibia by inserting a saw (not shown) onto cutting guide surface 204 and initiating first cut 12 through the anterior cortex and extending directly posteriorly through the posterior cortex of the proximal tibia. Accordingly first, second and third cutting guide surfaces 204, 208, 218 are partially formed so as to engage the saw blade to be used, as would be understood in the art. First cut 12 is extended as medially and as laterally as possible using the straight bone saw, which includes extending first cut 12 through the medial cortex of the tibia. First cut 12 is then continued by inserting osteotome 250 through first guide surface 204 and maneuvering the cutting portion 254 of the osteotome 250 behind the patella tendon. Guide arm 256 is then extended through guide hole 258a and is affixed to the cutting portion 254 in the body portion 252 as shown in FIG. 13. Osteotome 250 is then driven, by means known in the art, posteriorly until it penetrates the posterior cortex of the proximal tibia. Osteotome is then disassembled and removed from slot 204 and guide hole 258a. Cut 214 is then formed first by drilling a hole using osteotome guide hole 258b through to the posterior cortex of the proximal tibia. Referring now to FIG. 14, insert 206 is then engaged in receiving portion 204 of body 202. Second cut 14 is then formed in a similar fashion to the first cut by first using a straight bone saw and finishing the cut with L-shaped osteotome 250 using guide hole 258b to secure arm 256 (as shown in FIG. 15). Next, both the osteotome and first insert 206 are removed from tibia 10.

Figure 16:
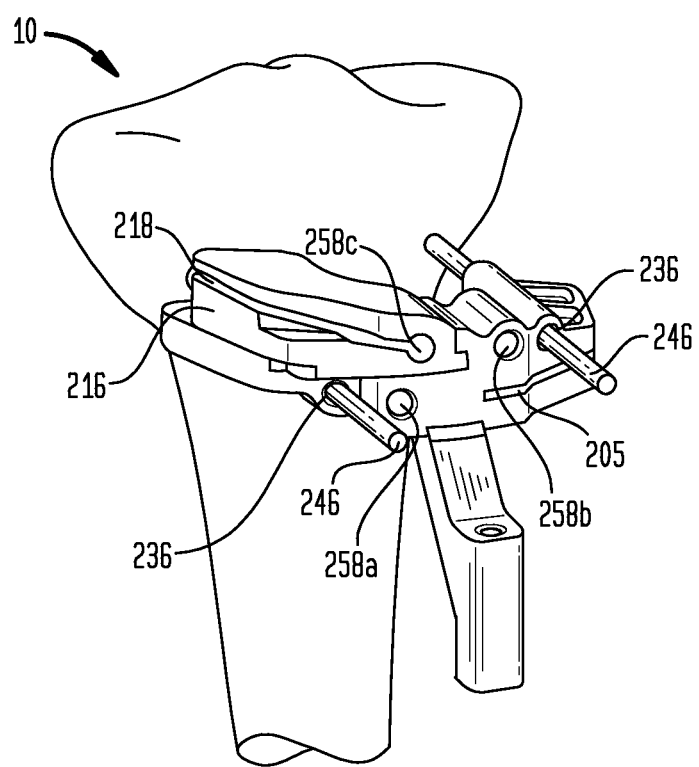
FIG. 16 is an isometric view of a tibia with the cutting block of FIG. 9 mounted thereto including the insert of FIG. 10 during step in a process according to an embodiment of the present invention.
Figure 17:
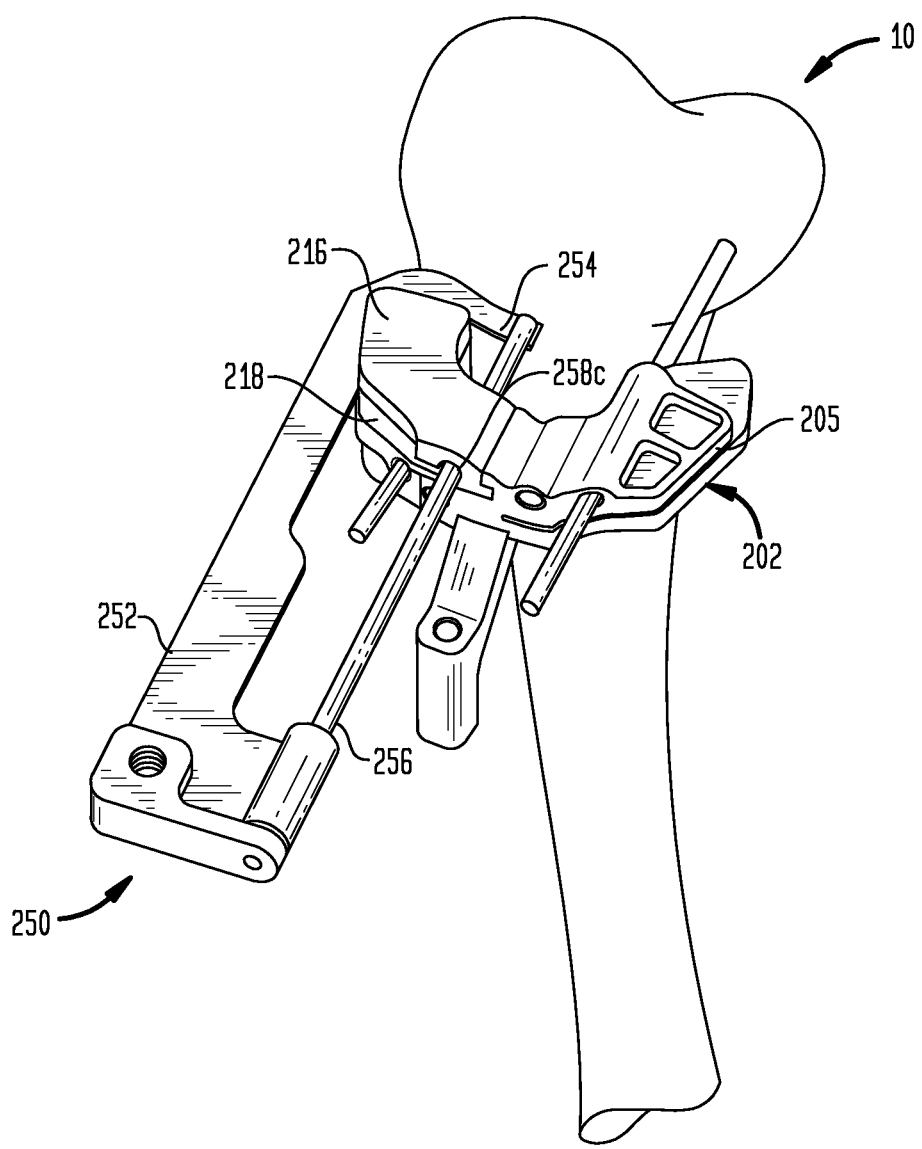
FIG. 17 is an isometric view of a tibia as shown in FIG. 16 with the osteotome of FIG. 11 inserted therein to finalize the second cut in the tibia.

As shown in FIGS. 16-17, third cut 16 is then formed by first sliding insert portion 216 into receiving portion 204 of body portion 202. As discussed above, third guide 218 is formed within insert portion 216 so as to be angled relative to first guide 205 of receiving portion 204 so as to provide the appropriate angle for third cut 16 corresponding to the appropriate amount of angular correction for the knee. In a preferred embodiment of the present invention, a number of different insert portions 216 of varying angles can be included in a kit with body portion 202 allowing the surgeon to select the appropriate insert which will correspond to the predetermined amount of angular correction. Guide hole 258c is then used to drill a hole 259c through tibia 10 to the posterior cortex thereof. Third cut 16 is then formed as discussed above in the same manner as first cut 12 and second cut 14 by initiating the cut with a straight bone saw and finishing the cut with osteotome 250. Third cut 16 may be formed so as to not extend behind the patella tendon; however, it may still be preferred to form third cut using osteotome 250. At this point all instruments are removed from the knee, including cutting block 200 and the osteotomy is completed as discussed above.

As shown in FIG. 18, autograft 18 is removed from tibia 10, forming closing wedge 26, into which implant 28 may be inserted. Preferably, cutting block 200 is formed so as to be used on the anterior portion of the proximal tibia, and accordingly will be formed along the posterior portion 230 so as to match the general profile of the anterior portion of the proximal tibia. Further, as shown in FIG. 8 body 202 includes a cutout or recessed area 232 formed in the posteriorly-facing surface thereof which allows cutting block to straddle the patellar tendon of the patient. If necessary, a corresponding cutout of recessed area 234 may be formed in first insert 206 and second insert 216.

Figure 19A:
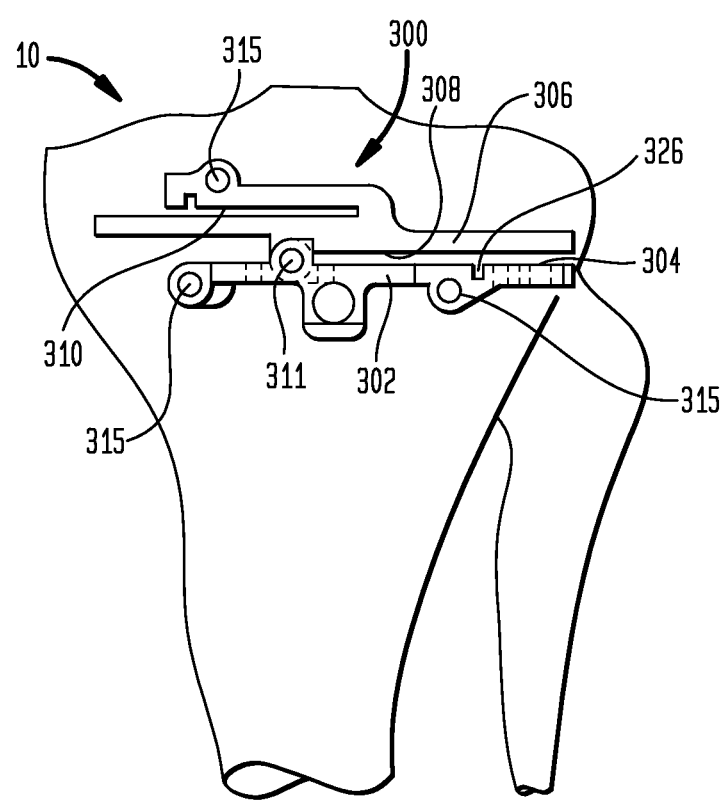
FIG. 19*a* is an anterior view of a tibia with a second embodiment of the cutting block mounted thereon in a first arrangement.
Figure 19B:
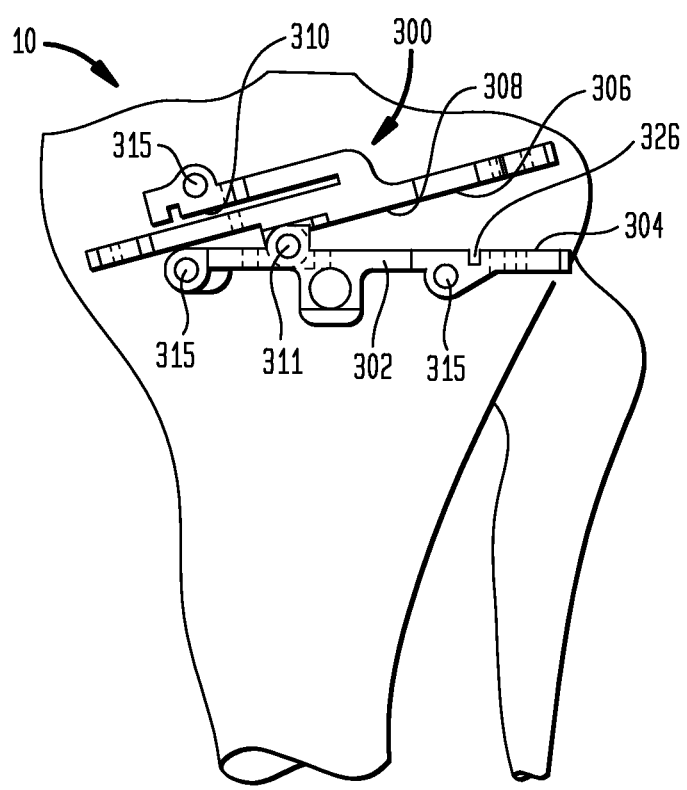
FIG. 19*b* is an anterior view of a tibia with a the embodiment of the cutting block shown in FIG. 19 mounted on the tibia in a second arrangement.
Figure 20:
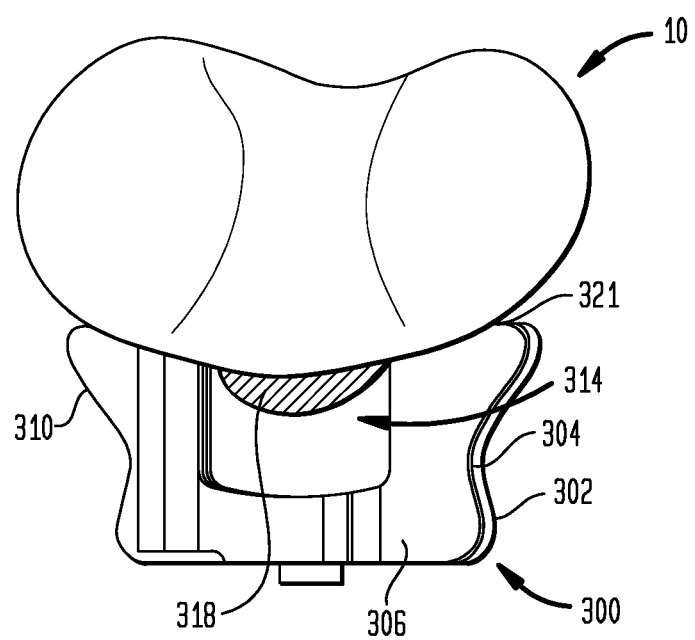
FIG. 20 is a top view of a tibia as shown in FIG. 19.
Figure 21:
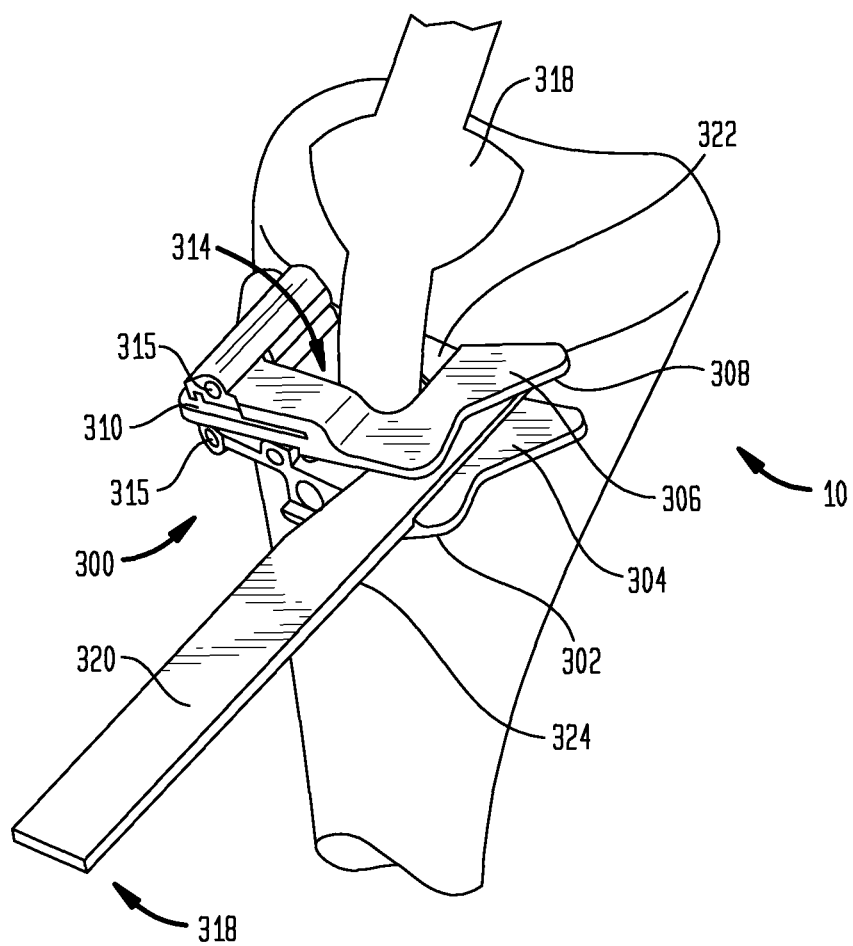
FIG. 21 an isometric view of a tibia with the second embodiment of the cutting block mounted thereon and a saw blade being used to make a first cut.

Referring now to FIGS. 19-21, an alternative cutting block 300 according to a further embodiment of the present invention is shown. Although the particular cutting block 300 shown in FIGS. 19-21 is shown as being adapted so as to form a pattern for first, second, and third cuts 112, 114, 116 as shown in FIG. 6-7, it is to be understood that one having reasonable skill in the art upon reading this disclosure could adapt such a cutting block 300 to perform other variations of the procedure according to further embodiments of the present invention, including those performed on the opposite knee or to correct a varus, as opposed to valgus, condition. As shown in FIGS. 19a and b, cutting block 300 has a first arm 302 having a first guide 304 formed therein to be used in making first cut 112. Cutting block 300 further includes a second arm 306 which is rotatably mounted to first arm 302 at a hinge with pivot pin 311, and includes second guide surface 308 and a third guide surface 310 formed therein. Each of second and third guide surfaces 308, 310 are structured so as to provide a guide for a bone saw used in forming second cut 114 and third cut 116, respectively. Second guide surface 308 and third guide surface 310 are arranged on second arm 306 to as to be substantially parallel to each other. Further, third guide surface 310 is positioned within second arm 306 so as to be proximal to second guide 308. Second and third guides 308, 310 are preferably positioned on opposites sides of second arm 306 in the medial-lateral direction so as to correspond to the preferred locations of second and third cuts 114, 116.

The rotational affixation of second arm 306 to first arm 302 about pivot pin allows for an infinite number of positions to be chosen in order to provide the desired angular correction for an HTO procedure according the embodiments of the present invention. Cutting block 300 is adapted to be affixed to the anterior portion of the proximal tibia, and accordingly includes a profile 312 that substantially matches that of a typical anterior proximal tibia. Cutting block 300 is further adapted to be used on the anterior portion of proximal tibia by incorporation of cutout 314 therein. As with cutout 232 of FIG. 8, cutout 314 is structured so as to allow cutting block 302 to straddle the patella tendon of the patient. Fixation of cutting block to the tibia is achieved by inserting fixation pins (not shown) into holes 315, 316 which are formed in cutting block 302.

A further aspect of the present invention includes a method for performing a high tibial osteotomy (HTO) procedure according to an embodiment of the present invention using cutting block 300. To begin the procedure, an incision is made near the knee of the patient to allow access to the anterior portion of the proximal tibia. Preferably a single cut is made, but optionally two cuts can be made, one medially and one laterally of patella tendon 340. Once access is gained to the proximal tibia, cutting block 300 is introduced to the tibia 10 through the incision and placed adjacent to the anterior proximal tibia such that cut out 314 straddles patella tendon 340 of the patient. First arm 302 of cutting block 300 is then aligned, preferably with first cutting guide surface 304 substantially parallel to the mechanical axis of the tibia, and secured to the tibia using a fixation pin inserted through hole 315 and into tibia 110 (as shown in FIG. 19a). Second arm 306 is then rotated about hinge 311 such that the angle between first cutting guide surface 304 and second guide 308 corresponds to the amount of angular correction required for the procedure (as shown in FIG. 19b). Second arm 306 is then affixed to the proximal tibia by inserting a fixation pin through hole 316 and into tibia 10.

Next, first cut 112 is made in the proximal tibia by initiating the cut with a straight bone saw with the aid of first guide 304. Interference with patella tendon of the patient may prevent first cut 312 from being made at the appropriate medial-lateral width with respect to the tibia using a straight bone saw. Accordingly, in order to make first cut 112 of the desired width, first cut 112 is finished using an osteotome as shown in FIG. 21. Osteotome 318 is shown as being generally L-shaped, having an elongated body portion 320 and a cutting portion 322 extending approximately perpendicular thereto. First cut 312 is completed using osteotome 318 by extending osteotome onto first guide surface 304 and manipulating end portion 322 around and behind patella tendon 340 of the patient. To ensure that first cut 112 is made at the appropriate width, osteotome 318 is formed having a guide arm 324 therein so as to substantially mate with guide slot 326 formed in cutting guide surface 304. When osteotome 318 is inserted into cutting guide surface 304 guide arm 324 is engaged with guide slot 326. Osteotome 318 is then advanced into the proximal tibia and through the posterior cortex thereof. Osteotome 318 is then removed from the width 110.

Second cut 314 and third cut 316 are formed in a similar fashion as with respect to first cut 312 by initiating the cut with a straight bone saw and finishing the cut with osteotome 318. Once the desired cuts have been made, cutting block 300 and fixation pins are removed from the knee and the surgery is completed as discussed above with reference to FIGS. 6 and 7.

Figure 26:
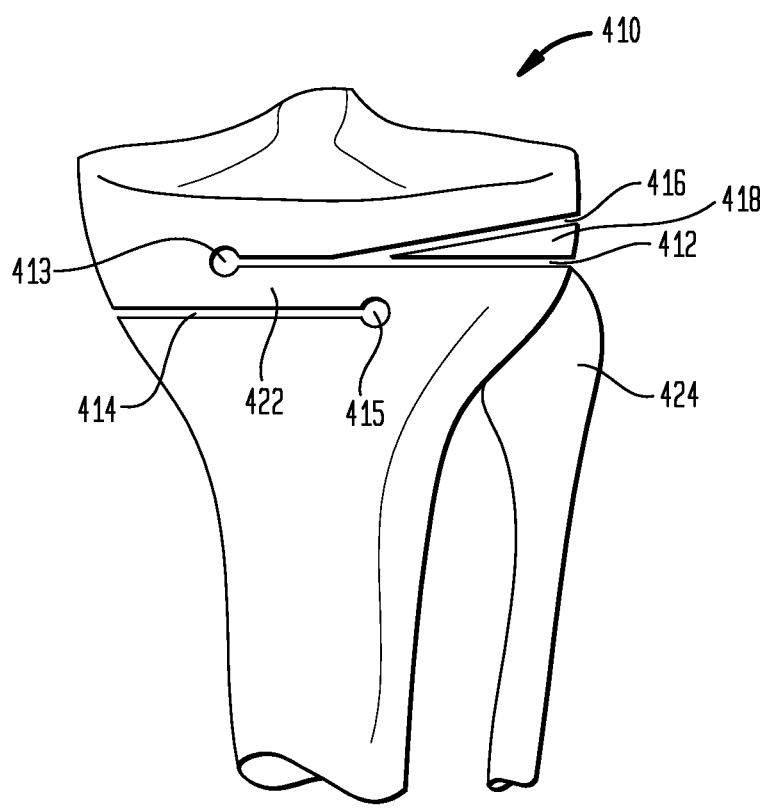
FIG. 26 is an anterior view of a proximal tibia during a step of a procedure showing three bone cuts according to an embodiment of the present invention.
Figure 27:
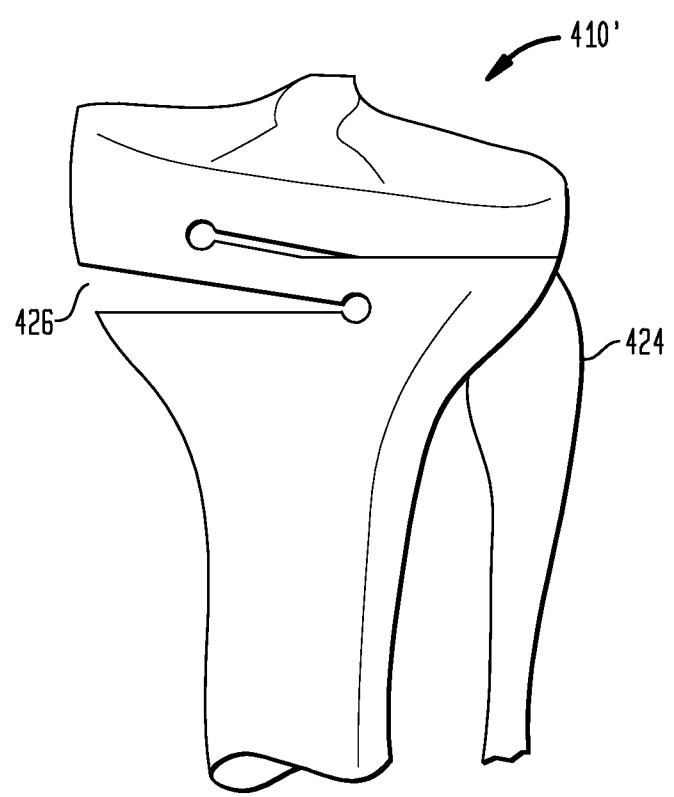
FIG. 27 is an anterior view of a proximal tibia during a step of a procedure showing rotation of the tibial head to close the opening created after removal of a bone wedge therefrom.

FIGS. 19-25 show an alternative embodiment of a cutting block system that can be used in completing an HTO procedure according to an embodiment of the present invention. In the particular embodiment illustrated, the procedure is one which is carried out to correct a valgus deformity in the proximal portion of a left tibia 410, as shown in FIG. 26. In such a procedure, a cutting pattern similar to that which is shown in FIG. 27 is made in the proximal tibia 410. This pattern includes a first cut 412, a second cut 414 and a third cut 416 which produces a removable, wedge-shaped section 418 of bone that can be removed from the proximal tibia 410. It is noted that, although ordinal designations are given to the cuts described herein as being made in the proximal tibia, such designations are made for convenience only and are not intended to limit the scope of the invention described herein.

Figure 22:
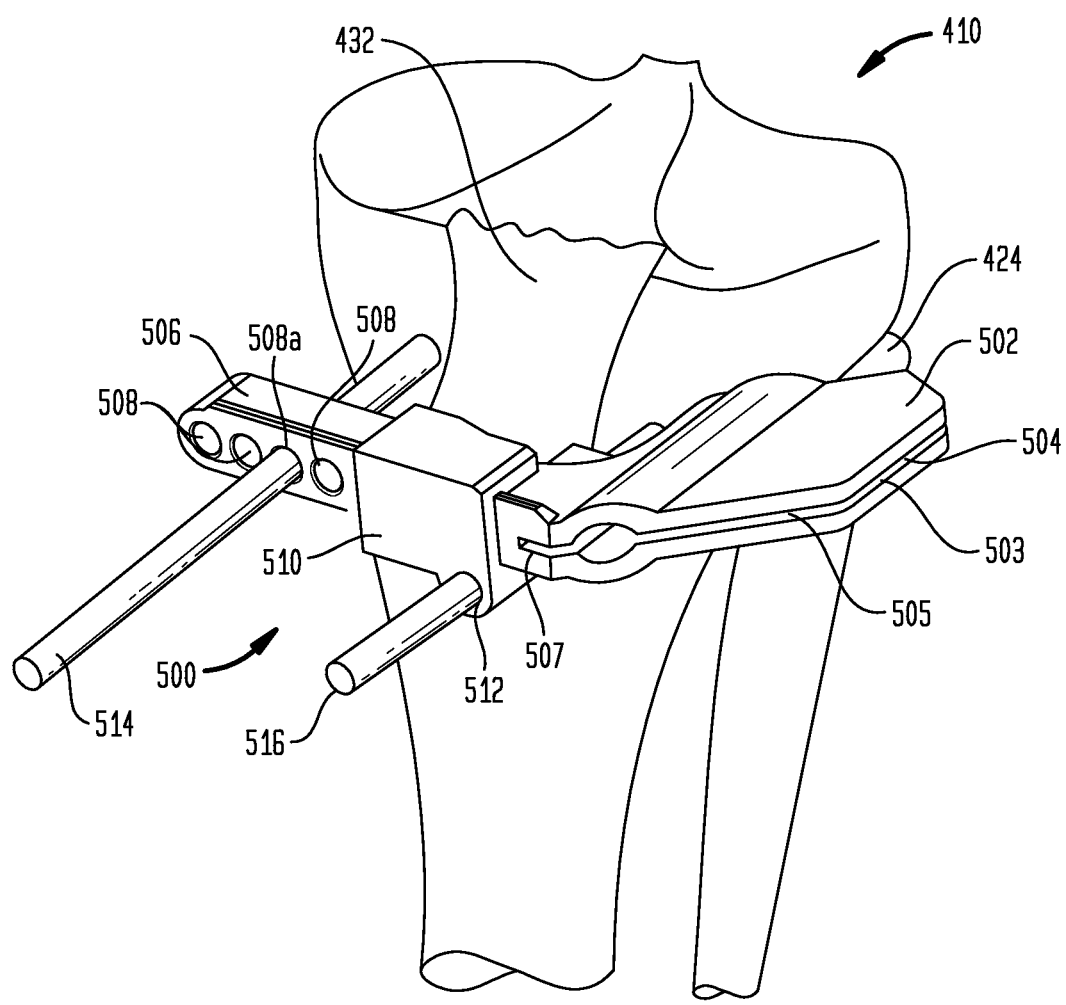
FIG. 22 is an isometric view of a tibia with a first cutting block of a system according to a further embodiment of the present invention attached thereto in a first position.

The cutting block system of the current embodiment includes a first cutting block 500, shown in FIG. 22. First cutting block 500 includes a cutting guide portion 502 which includes a first cutting guide surface 504 formed therein. Cutting guide surface 504 is generally planar and preferably (as shown in FIG. 22) includes a top portion 503 and a bottom portion 505 such that it is capable of surrounding a cutting instrument, such as an oscillating saw, osteotome or other similarly suitable instrument, on both a top side and a bottom side thereof. First cutting block 500 also includes arm 506 that extends from the cutting guide portion 502 in a direction that lies along a plane formed by the cutting guide surface 504. Arm 506 includes a plurality of holes 508 extending therethrough in a direction substantially orthogonal thereto. Furthermore, first cutting block 500 includes a sliding member 510 that is slideably engaged on arm 506. Sliding member 510 includes hole 512 formed therein that is substantially parallel to the holes 508 formed in arm 506.

Figure 24:
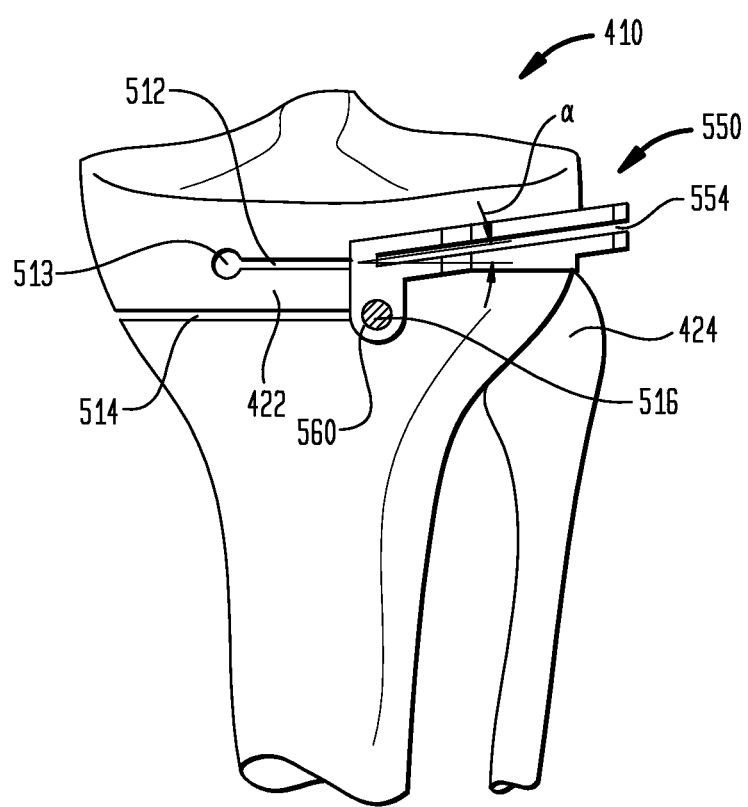
FIG. 24 is a front view of a tibia with a second cutting block from the system of the present embodiment attached thereto.
Figure 25:
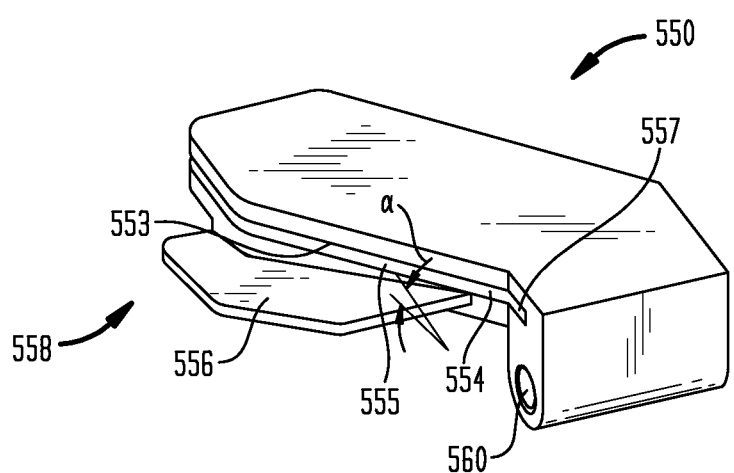
FIG. 25 is an isometric view of the second cutting block shown in FIG. 24.

The cutting block system of the present embodiment also includes a second cutting block 550, which is shown in FIG. 24. Second cutting block 550 includes second cutting guide surface 554 which, in the particular embodiment illustrated in FIG. 24 is shown as having both a top portion 553 and a bottom portion 555, each being substantially planar and open to the other. In this manner, second cutting guide surface 554 is capable of surrounding a suitable cutting instrument from both the top and bottom. Such an arrangement is preferable because it may improve the accuracy with which the desired cuts are made. Second cutting block 550 further includes flange 556 which projects from posterior surface 558 of second cutting block 550. Flange is a generally planar structure having an elongate width and depth. Flange 556 is arranged at an angle α with respect to second cutting guide surface 554 such that second cutting block 550 can be used to form third cut 416 in proximal tibia 410.

In a method of using this embodiment of the present invention (discussed with reference to FIGS. 22-27), a first pin 514 and a second pin 516 are inserted into the proximal tibia, preferably by first drilling a hole into the proximal tibia in the desired location for each pin and then by press-fitting the pins 514, 516 into the hole. The desired location for first pin 514 is preferably along a line directed substantially in the anterior-posterior direction that is located along the desired terminal end 413 of first cut 412 (as shown in FIG. 26). Similarly, second pin 516 is inserted into the proximal tibia 410 in a location that is preferably along a line directed substantially in the anterior-posterior direction that is located along the desired terminal end 415 of second cut 414.

Once first 514 and second 516 pins are in place, first cutting block 500 is assembled onto pins 514, 516 in the position shown in FIG. 22. In this position, first cutting guide surface 504 is positioned substantially on the lateral side of the left tibia 410. In this orientation, the plurality of holes 508 within arm 506 are located proximally of hole 512 within sliding member 510. First cutting block 500 is assembled in this position onto proximal tibia 410 by first aligning one of the plurality of holes 508 disposed within arm 506 with first pin 514. The hole 508a aligned with pin 514 is selected so that proper alignment of first cutting guide surface 504 relative to the lateral side of tibia 410 is achieved. In such an alignment, the closed end 507 of cutting guide surface is located just laterally of patellar tendon 432, the contour of cutting guide portion 502 follows as closely as possible the profile of the tibia 410, and arm 506 is spaced anteriorily apart from patellar tendon 432. Once the proper hole 508a is selected, it is aligned with first pin 514. Next, hole 512 disposed within sliding member 510 is aligned with second pin 516 by moving sliding member 510 along arm 506 to the required location. Once alignment of holes 508a, 512 with respect to first pin 514 and second pin 516 has been completed, first cutting block 500 is slid along pins 514, 516 until cutting guide portion 502 contacts a portion of the surface of proximal tibia 410. Proper alignment of first cutting guide surface 504 with respect to the desired location of first cut 512 is achieved by spacing apart first pin 514 and second pin 516 from one another in the proximal-distal direction by the same distance as that by which holes 508 in arm 506 are spaced apart from hole 512 in sliding member 510 in the same direction. This direction should be equal to the desired thickness for the bone hinge section 434 (shown in FIGS. 26 and 27). Preferably, bone hinge section 434 should be thick enough so as to not fracture during post-operative recovery, but thin enough so as not to break, particularly in response to an applied torsional load, during subsequent rotation of the tibial plateau.

Once first cutting block is properly affixed to proximal tibia 410 in the proper position, first cut 412 is formed using a cutting instrument, preferably in the form of an oscillating bone saw, in connection with first cutting guide surface 504. Preferably, first cut 412 is started by driving the cutting instrument in a generally posterior direction, with an edge thereof substantially abutted against the closed end 507 of first cutting guide 504. Because closed end 507 is placed laterally of the patellar tendon 434, this procedure allows first cut 412 to be started without interference with the patellar tendon 434. Once first cut 412 is started in this manner, it may be finished by rotating the cutting instrument around and behind the patellar tendon. This rotation is accommodated by the proximally-extending shape of cutting guide portion 502, which allows for the cutting instrument to be manipulated behind patellar tendon 434 while maintaining contact with first cutting guide surface 504. Although, depending on the particular procedure by which the cutting block system of the present invention is used, the end of first cut 413 may be blind, the placement of first pin 514 at the desired location for the end 413 of first cut 412 allows first pin 514 to act as a stop for the cutting instrument.

That is, the presence of first pin 514 effectively limits the medial distance to which first cut 412 can be made.

Figure 23:
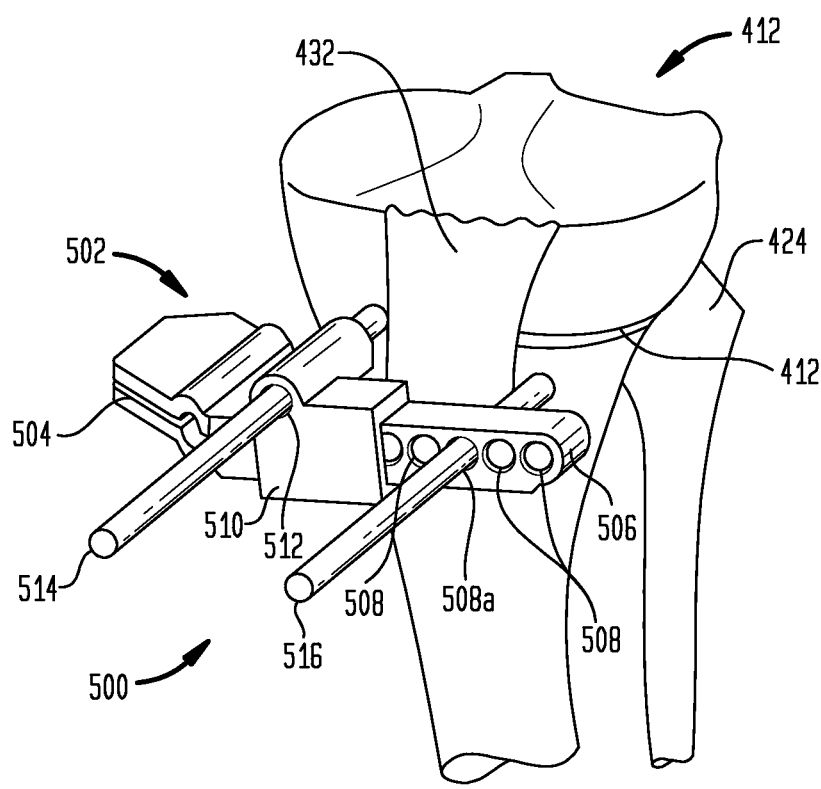
FIG. 23 is an isometric view of a tibia with the cutting block shown in FIG. 22 attached thereto in a second position.

Once first cut 412 is completed, first cutting block 500 is removed from the proximal tibia 410 by sliding first cutting block 500 in an anterior direction on pins 514, 516. First cutting block is then rotated into a second position, as shown in FIG. 23, and re-engaged with pins 514, 516 in such a position. The assembly of the first cutting block 500 onto first and second pins 514, 516 in this second position is similar to the assembly thereof in the first position. In this manner, one of the holes 508a in arm 506 is properly aligned with second pin 516 and hole 512 in sliding member 510 is aligned with first pin 514, then first cutting block 500 is slid into contact with the anterior portion of proximal tibia 410. In this position, first cutting guide surface 504 is directed toward the medial side of the proximal tibia 410, and is aligned in the desired location for second cut 414. In this position, the fact that the holes 508 in arm 506 are aligned substantially on the plane defined by first cutting guide surface 504 serves to align first cutting guide surface in the proper position for second cut such that second pin 516 is located at the terminal end 415 thereof. Once first cutting block 500 is appropriately positioned, a cutting instrument is used to form second cut 414 in a similar manner to that which is described above with respect to the formation of first cut 412.

Once second cut 414 is formed in the above-described manner, first cutting block 500 is removed from the proximal tibia 410 by sliding first cutting block 500 in a generally anterior direction to disengage pins 514, 516 from holes 508a, 512. Subsequently, second cutting block 550 is introduced and affixed to the proximal tibia 410. This is accomplished by aligning hole 560 formed in second cutting block 550 with second pin 516 and sliding second cutting guide 550 on second pin 516 until it comes into engagement with the anterior portion of the proximal tibia 410. As this is done, flange 556 is aligned with and inserted into first cut 412. The insertion of flange 556 into first cut 412 serves to properly orient second cutting guide surface 554 at angle α with respect to first cut. Angle α preferably corresponds to a predetermined angle of correction that is desired for the particular bone being operated upon, and may be determined by methods known in the art. Generally, multiple variations of second cutting block 550 can be made, each having different values for α formed therein. Such variations of second cutting block 550 can be provided in a kit from which a surgeon performing an operation according to an embodiment of the present invention, having determined an appropriate value for α, can select an appropriate variation of second cutting block 550.

Once second cutting block 550, having an appropriate value for α is assembled onto the proximal tibia 410, third cut 416 is made using a cutting instrument, preferably in the form of an oscillating bone saw on second cutting guide surface 554. Closed end 557 of second cutting guide surface 554 is preferably located laterally of the patellar tendon 434 when second cutting block 550 is properly affixed to proximal tibia 410. Accordingly, third cut 416 can be made by driving a cutting instrument in a substantially posterior direction along closed end 557 of second cutting guide surface 554. Preferably terminal 557 of second cutting guide surface 554 is located within second cutting block 550 such that it is positioned within a point along first cut 512. It is further preferred that closed end 557 does not extend distally of first cut 512. After completion of third cut 516, a removable wedge-shaped section 418 remains, which is removed from proximal tibia 410. The procedure is then completed in a similar manner as that which is described with respect to other embodiments of the present invention.

Although the method of the present embodiment has been discussed with respect to use of a cutting block, as shown and described with respect to the various figures herein, in completing an HTO procedure to correct for a varus deformity, it would be understood by one having reasonable skill in the art that a cutting block could be used in an HTO procedure for correcting a valgus deformity. Further, although the present invention has been discussed with respect to an osteotomy procedure performed on the knee of a patient, and more specifically the proximal tibia of the patient, it would be understood to one having reasonable skill in the art that such procedure can be used in connection with other joints of the human body. Such joints include, but are not limited to, the elbow and wrist.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A cutting block for use in a bone osteotomy procedure on a proximal portion of a tibia, the tibia having a longitudinal axis, and the tibia having a first side on one side of a patella tendon and a second side on another side of the patella tendon, the cutting block comprising:
   a. a first cutting guide surface open to a first side of said cutting block, said first cutting guide surface extending from the first side of the cutting block towards a central portion of the cutting block, the first cutting guide surface terminating in the central portion at a first stop surface transversely oriented to the first cutting guide surface;
   b. a second cutting guide surface open to a second side of said cutting block, said second cutting guide surface extending from the second side of the cutting block towards the central portion of the cutting block, the second cutting guide surface terminating in the central portion at a second stop surface transversely oriented to the second cutting guide surface;
   c. a third cutting guide surface open to the second side of the cutting block; and
   d. a cutout portion defining a recess adapted to receive the patella tendon by straddling the patella tendon such that the cutting block contacts the proximal portion of the tibia on both the first and second sides of the patella tendon;
   wherein the cutting block is adapted to be temporarily affixed to an anterior portion of the proximal portion of the tibia in an affixed position, such that, when the patella tendon is received by the recess of the cutout portion, said first cutting guide surface is disposed on the first side of the tibia defining a first plane with respect to the tibia, the second cutting guide surface is disposed on the second side of the tibia defining a second plane with respect to the tibia, and the third cutting guide surface is disposed on the second side of the tibia defining a third plane with respect to the tibia, the second and third planes intersecting at an angle within the tibia to form an apex, and wherein said first and second cutting guide surfaces are disposed on a first arm.

2. The cutting block of claim 1, wherein said third cutting guide surface is disposed on a second arm, said second arm being rotatably affixed to said first arm.

3. The cutting block of claim 2 further comprising a first hole formed in said first arm adapted to accept a first pin temporarily affixed to said proximal portion of said tibia.

4. The cutting block of claim 3 further comprising a second hole formed in said second arm adapted to accept a second pin that is temporarily affixed to said proximal portion of said tibia.

5. The cutting block of claim 4, wherein, in the affixed position, the first and second holes extend along an anterior-posterior direction.

6. The cutting block of claim 1, wherein said first cutting guide surface and said second cutting guide surface are disposed on said first arm in a parallel relationship to each other.

7. The cutting block of claim 6, wherein said first cutting guide surface is proximal to said second cutting guide surface.

8. The cutting block of claim 1, wherein said first cutting guide surface is used to form a first cut in said proximal tibia, said second cutting guide surface is used to form a second cut in said proximal tibia, and said third cutting guide surface is used to form a third cut in said proximal tibia, each of said first, second, and third cuts having a terminal end.

9. The cutting block of claim 8, wherein said terminal ends of said first and second cuts form an overlap therebetween.

10. The cutting block of claim 1, wherein said first cutting guide surface, said second cutting guide surface and said third cutting guide surface are adapted for use with an osteotome.

11. The cutting block of claim 10, wherein said osteotome is L-shaped.

12. The cutting block of claim 10 further comprising:
a. a first slot formed in said first cutting guide surface;
b. a second slot formed in said second cutting guide surface; and
c. a third slot formed in said third cutting guide surface;
wherein said first, second, and third slots are adapted to mate with a guide arm formed on said osteotome.

13. The cutting block of claim 1, wherein the cutting block has a curved surface that substantially conforms to a profile of the anterior portion of the tibia.

14. The cutting block of claim 1, wherein the cutting block is structured such that the entirety of the cutting block is positioned on an anterior side of the anterior portion of the tibia when the cutting block is in the affixed position.

15. The cutting block of claim 1, wherein said third cutting guide surface extends from the second side of the cutting block towards the central portion of the cutting block, the third cutting guide surface terminating in the central portion.

16. The cutting block of claim 1, wherein the first and second stop surfaces are positioned such that the first and second cutting guide surfaces overlap in the central portion of the cutting block.

17. A cutting block for use in a high-tibial osteotomy procedure, comprising:

a. a first arm having a first cutting guide surface and a second cutting guide surface disposed therein, said first cutting guide surface extending from a first side of the cutting block towards a central portion of the cutting block, and said second cutting guide surface extending from a second side of the cutting block towards the central portion of the cutting block, the first cutting guide surface terminating in the central portion at a first stop surface transversely oriented to the first cutting guide surface, and the second cutting guide surface terminating in the central portion at a second stop surface transversely oriented to the second cutting guide surface, said first arm having a first hole formed therein, the first hole adapted to accept a first pin temporarily affixed to an anterior portion of a proximal tibia, the anterior portion of the proximal tibia having a first side on one side of a patella tendon and a second side on another side of the patella tendon;

b. a second arm having a third cutting guide surface disposed thereon, said second arm being rotatably affixed to said first arm, said second arm having a second hole formed therein, the second hole adapted to accept a second pin temporarily affixed to the anterior portion of the proximal tibia; and c. a cutout portion defining a recess adapted to receive the patella tendon by straddling the patella tendon such that the cutting block contacts the proximal portion of the tibia on both the first and second sides of the patella tendon;

wherein said cutting block is adapted to be temporarily affixed to the anterior portion of the proximal tibia in an affixed position in which said patella tendon is received by said recess of said cutout portion and the entirety of said cutting block is positioned on an anterior side of the anterior portion of the proximal tibia, wherein, in the affixed position, said first cutting guide surface is disposed on said first side of said proximal tibia, said second cutting guide surface is disposed on said second side of said proximal tibia, and said third cutting guide surface is disposed on said second side of said proximal tibia, and wherein, in the affixed position, the first and second holes extend along an anterior-posterior direction; and wherein said first cutting guide surface and said second cutting guide surface are substantially parallel to each other.

18. The cutting block of claim 17, wherein the cutting block has a curved surface that substantially conforms to a profile of the anterior portion of the proximal tibia.

19. The cutting block of claim 17, wherein said third cutting guide surface extends from the second side of the cutting block towards the central portion of the cutting block, the third cutting guide surface terminating in the central portion.

20. The cutting block of claim 17, wherein the first and second stop surfaces are positioned such that the first and second cutting guide surfaces overlap in the central portion of the cutting block.

* * * * *